(12) United States Patent
Benatuil et al.

(10) Patent No.: US 9,458,244 B2
(45) Date of Patent: Oct. 4, 2016

(54) SINGLE CHAIN MULTIVALENT BINDING PROTEIN COMPOSITIONS AND METHODS

(71) Applicant: AbbVie, Inc., Worcester, MA (US)

(72) Inventors: Lorenzo Benatuil, Northborough, MA (US); Chung-Ming Hsieh, Newton, MA (US)

(73) Assignee: AbbVie Inc., North Chicago, IL (US)

(*) Notice: Subject to any disclaimer, the term of this patent is extended or adjusted under 35 U.S.C. 154(b) by 195 days.

(21) Appl. No.: 14/141,500

(22) Filed: Dec. 27, 2013

(65) Prior Publication Data

US 2014/0221621 A1 Aug. 7, 2014

Related U.S. Application Data

(60) Provisional application No. 61/746,659, filed on Dec. 28, 2012.

(51) Int. Cl.
| | |
|---|---|
| *C40B 40/10* | (2006.01) |
| *C07K 16/46* | (2006.01) |
| *C07K 16/22* | (2006.01) |
| *C07K 16/24* | (2006.01) |

(52) U.S. Cl.
CPC .............. *C07K 16/468* (2013.01); *C07K 16/22* (2013.01); *C07K 16/241* (2013.01); *C07K 2317/626* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 5,624,821 | A | 4/1997 | Winter et al. |
| 5,641,870 | A | 6/1997 | Rinderknecht et al. |
| 5,648,260 | A | 7/1997 | Winter et al. |
| 5,714,350 | A | 2/1998 | Co et al. |
| 6,350,861 | B1 | 2/2002 | Co et al. |
| 6,699,658 | B1 | 3/2004 | Wittrup et al. |
| 8,258,268 | B2 | 9/2012 | Wu et al. |
| 2002/0137134 | A1 | 9/2002 | Gerngross |
| 2004/0018590 | A1 | 1/2004 | Gerngross et al. |
| 2007/0071675 | A1 | 3/2007 | Wu et al. |
| 2011/0076752 | A1 | 3/2011 | Wu et al. |
| 2012/0237442 | A1 | 9/2012 | Rossi et al. |

FOREIGN PATENT DOCUMENTS

| | | |
|---|---|---|
| EP | 1176195 B1 | 5/2013 |
| EP | 2 647 704 A1 | 10/2013 |
| WO | 9905144 A1 | 5/1990 |
| WO | 9954342 A1 | 10/1999 |
| WO | 0177342 A1 | 10/2001 |

(Continued)

OTHER PUBLICATIONS

Kriangkum et al. 'Bispecific and Bifunctional Single Chain Recombinant Antibodies'. Biomolecular Engineering. 2001, vol. 18, No. 2, pp. 31-40.

(Continued)

*Primary Examiner* — Christian Boesen
(74) *Attorney, Agent, or Firm* — Lathrop & Gage LLP; James H. Velema, Esq.

(57) ABSTRACT

Provided are protein, nucleic acid, and cellular libraries of single chain multivalent binding proteins (e.g., scDVD and scDVDFab molecules) and methods of using these of these libraries for the screening of single chain multivalent binding proteins using cell surface display technology (e.g., yeast display).

31 Claims, 29 Drawing Sheets

(56) References Cited

FOREIGN PATENT DOCUMENTS

| WO | 02/00729 A2 | 1/2002 |
|---|---|---|
| WO | 03016466 A2 | 2/2003 |
| WO | 03035835 A2 | 5/2003 |
| WO | 2005100584 A2 | 10/2005 |
| WO | 2007/048037 A2 | 4/2007 |
| WO | 2012/074029 A1 | 6/2012 |
| WO | 2012/088302 A2 | 6/2012 |
| WO | 2012/135345 A1 | 10/2012 |
| WO | 2013/063114 A1 | 5/2013 |

OTHER PUBLICATIONS

Lu et al. 'Simultaneous Blockade of Both the Epidermal Growth Factor Receptor and the Insulin-like Growth Factor Receptor Signaling Pathways in Cancer Cells with a Fully Human Recombinant Bispecific Antibody'. The Journal of Biological Chemistry. 2004, vol. 279, No. 4, pp. 2856-2865.

Miller et al. 'Design, Construction, and In Vitro Analyses of Multivalent Antibodies'. The Journal of Immunology. 2003, vol. 170, No. 9, pp. 4854-4861.

Huber et al. 'Cystallographic Structure Studies of an IgG Molecule and an Fc Fragment'. Nature. 1976, vol. 264, pp. 415-420.

Thies et al. 'Folding and Association of the Antibody Domain CH3: Prolyl Isomerization Preceeds Dimerization'. Journal of Molecular Biology. 1999, vol. 293, pp. 67-79.

Dall'Acqua et al. 'Contribution of Domain Interface Residues to the Stability of Antibody CH3 Domain Homodimers'. Biochemistry. 1998, vol. 37, pp. 9266-9273.

Seligmann et al. 'Immunochemical Study of a Human Myeloma IgG1 Half Molecule'. Ann. Immunol. 1978, vol. 129, pp. 855-870.

Biewenga et al. 'IgA1 Half Molecules in Human Multiple Myeloma and the in vitro Production of Similar Fragments from Intact IgA1 Molecules'. Clinical and Experimental Immunology. 1983, vol. 51, pp. 395-400.

West et al. 'Crystal Structure and Immunoglobulin G Binding Properties of the Human Major Histocompatibility Complex-Related Fc Receptor'. Biochemistry. 2000, vol. 39, pp. 9698-9708.

Kim et al. 'Identifying Amino Acid Residues that Influence Plasma Clearance of Murine IgG1 Fragments by Site-directed Mutagenesis'. European Journal of Immunology. 1994, vol. 24, pp. 542-548.

Bird et al. 'Single-Chain Antigen-Binding Proteins'. Science. 1988, vol. 242, pp. 423-426.

Huston et al. 'Protein Engineering of Antibody Binding Sites: Recovery of Specific Activity in an Anti-digoxin Single-chain Fv Analogue Produced in *Escherichia coli*'. PNAS. 1988, vol. 85, pp. 5879-5883.

Holliger et al. '"Diabodies": Small Bivalent and Bispecific Antibody Fragments'. PNAS. 1993, vol. 90, pp. 6444-6448.

Poljak et al. 'Production and Structure of Diabodies'. Structure. 1994, vol. 2, pp. 1121-1123.

Zapata et al. 'Engineering Linear F(ab')2 Fragments for Efficient Production in *Escherichia coli* and Enhanced Antiproliferative Activity'. Protein Engineering. 1995, vol. 8, No. 10, pp. 1057-1062.

Kabat et al. 'Unusual Distributions of Amino Acids in Complementarity-determining (Hypervariable) Segments of Heavy and Light Chains of Immunoglobulins and Their Possible Roles in Specificity of Antibody-combining Sites* '. The Journal of Biological Chemistry. 1977, vol. 252, pp. 6609-6616.

Chothia et al. 'Canonical Structures for the Hypervariable Regions of Immunoglobulins'. Journal of Molecular Biology. 1987, vol. 196, pp. 901-917.

MacCallum et al. 'Antibody-antigen Interactions: Contact Analysis and Binding site Topography'. Journal of Molecular biology. 1996, vol. 262, pp. 732-745.

Shields et al. 'Lack of Fucose on Human IgG1 N-Linked Oligosaccharide Improves Binding to Human FcγRIII and Antibody-dependent Cellular Toxicity'. Journal of Biological Chemistry. 2002, vol. 277, pp. 26733-26740.

Umana et al. 'Engineered glycoforms of an antineuroblastoma IgG1 with optimized antibody dependent cellular cytotoxic activity'. Nature Biotechnology. 1999, vol. 17, pp. 176-180.

Urlaub et al. 'Isolation of Chinese Hamster Cell Mutants Deficient in Dihydrofolate Reductase Activity'. PNAS. 1980. vol. 77, No. 7, pp. 4216-4220.

Kaufman et al. 'Amplification and Expression of Sequences Cotransfected with a Modular Dihydrofolate Reductase Complementary DNA Gene'. Journal of Molecular Biology. 1982, vol. 159, pp. 601-621.

Benatuil et al. (2010) "An improved yeast transformation method for the generation of very large human antibody ibraries," Protein Engineering Design and Selection. 23(4):155-159.

Benhar (2007) "Design of synthetic antibody libraries," Expert Opinion on Biological Therapy. 7(5):763-779.

Caravella et al. (2010) "Design of next-generation protein therapeutics," Curr. Opin. Chem. Biol. 14(4):520-528.

Gunasekaran et al. (2010) "Enhancing Antibody Fc Fleterodimer Formation through Electrostatic Steering Effects," J. Biol. Chem. 285(25):19637-19646.

Holliger et al. (2005) "Engineered antibody fragments and the rise of single domains," Nat. Biotechnol. 23(9)1126-1136.

Hoogenboom (2005) "Selecting and screening recombinant antibody libraries," Nat. Biotechnol. 23(9):1105-1116.

Hornig et al. (Jan. 1, 2012) "Production of Bispecific Antibodies: Diabodies and Tandem scFv," Ch. 40 In; Antibody Engineering:Methods and Protocols. 2nd Ed. pp. 713-727.

Hudson et al. (2003) "Engineered antibodies," Nat. Med. 9(1):129-134.

Klein et al. (Nov. 1, 2012) "Progress in overcoming the chain association issue in bispecific heterodimeric IgG antibodies," mAbs. 4:653-663.

Kontermann (Mar. 1, 2012) "Dual targeting strategies with bispecific antibodies," mAbs. 4(2):182-197.

Larman et al. (Oct. 11, 2012) "Construction of a rationally designed antibody platform for sequencing-assisted selection," Proc. Natl. Acad. Sci. USA. 109(45):18523-18528.

Leong et al. (2008) "Preparing recombinant single chain antibodies," Chemical Engineering Science. 63(6):1401-1414.

Lu et al. (Dec. 26, 2012) "Frontier of therapeutic antibody discovery: the challenges and how to face them," World Journal of Biological Chemistry. 3(12)187-196.

Mack et al. (1995) "A small bispecific antibody construct expressed as a functional single-chain molecule with high tumor cell cytotoxicity," Proc. Natl. Acad. Sci. USA. 92(15):7021-7025.

Nagorsen et al. (Dec. 1, 2012) "Blinatumomab: a historical perspective," Pharmacology & Therapeutics. 136(3):334-342.

Presta et al. (2008) "Molecular engineering and design of therapeutic antibodies," Current Opinion in Immunology. 20(4):460-470.

Rajpal et al. (2005) "A general method for greatly improving the affinity of antibodies by using combinatorial libraries," Proc. Natl. Acad. Sci. USA. 102(24):8466-8471.

Schafer et al. (Jul. 5, 2011) "Immunoglobulin domain crossover as a generic approach for the production of bispecific IgG antibodies," Proc. Natl. Acad. Sci. USA. 108(27):11187-11192.

Sidhu et al. (2004) "Phage-displayed Antibody Libraries of Synthetic Heavy Chain Complementarity Determining Regions," J. Mol. Biol. 338(2):299-310.

Thiery et al. (Aug. 7, 2012) "Targeted multiplex imaging mass spectrometry with single chain fragment variable (SCFV) recombinant antibodies," Journal of the American Society for Mass Spectrometry. 23(10):1689-1696.

Walker et al. (2009) "Efficient recovery of high-affinity antibodies from a single-chain Fab yeast display library," J. Mol. Biol. 389(2):365-375.

Weaver-Feldhaus et al. (2004) "Yeast mating for combinatorial Fab library generation and surface display," FEBS Letters. 564(1):24-34.

Wolf et al. (2005) "BiTEs: bispecific antibody constructs with unique anti-tumor activity," Drug Discovery Today. 10(18):1237-1244.

International Search Report with Written Opinion corresponding to International Patent Application No. PCT/US2013/077912, mailed Jul. 16, 2014.

International Search Report with Written Opinion corresponding to International Patent Application No. PCT/US2013/077933, mailed Jan. 8, 2014.

*Figure 7B*

| Linker | Initial Library (%) | R2 (%) | Enrichment Folds Pos | Enrichment Folds neg |
|---|---|---|---|---|
| SL11 | 0.0 | 1.4 | - | - |
| SL9 | 5.3 | 7.1 | 1.4 | |
| SL7 | 9.2 | 8.6 | | 1.1 |
| SL5 | 14.5 | 2.9 | | 5.1 |
| GS11 | 2.6 | 2.9 | 1.1 | |
| GS9 | 11.8 | 1.4 | | 8.3 |
| GS7 | 13.2 | 2.9 | | 4.6 |
| GS5 | 9.2 | 1.4 | | 6.4 |
| RL11 | 3.9 | 25.7 | 6.5 | |
| RL9 | 5.3 | 17.1 | 3.3 | |
| RL7 | 10.5 | 18.6 | 1.8 | |
| RL5 | 11.8 | 7.1 | | 1.7 |

| Type of Linker | Initial Library (%) | R2 (%) | Enrichment Folds Pos | Enrichment Folds neg |
|---|---|---|---|---|
| SL | 28.9 | 20.0 | - | 1.4 |
| GS | 36.8 | 8.6 | | 4.6 |
| RL | 31.6 | 68.6 | 2.2 | |

STEP 1 - synthesize DNA sequences and assemble using PCR overlap

STEP 1 - synthesize DNA sequences and assemble using PCR overlap

STEP 2 – Linearize yeast vector, electroporate vector and each library independently, yeast circularizes libraries by homologous recombination, propagate yeast so each becomes a clone expressing one sequence

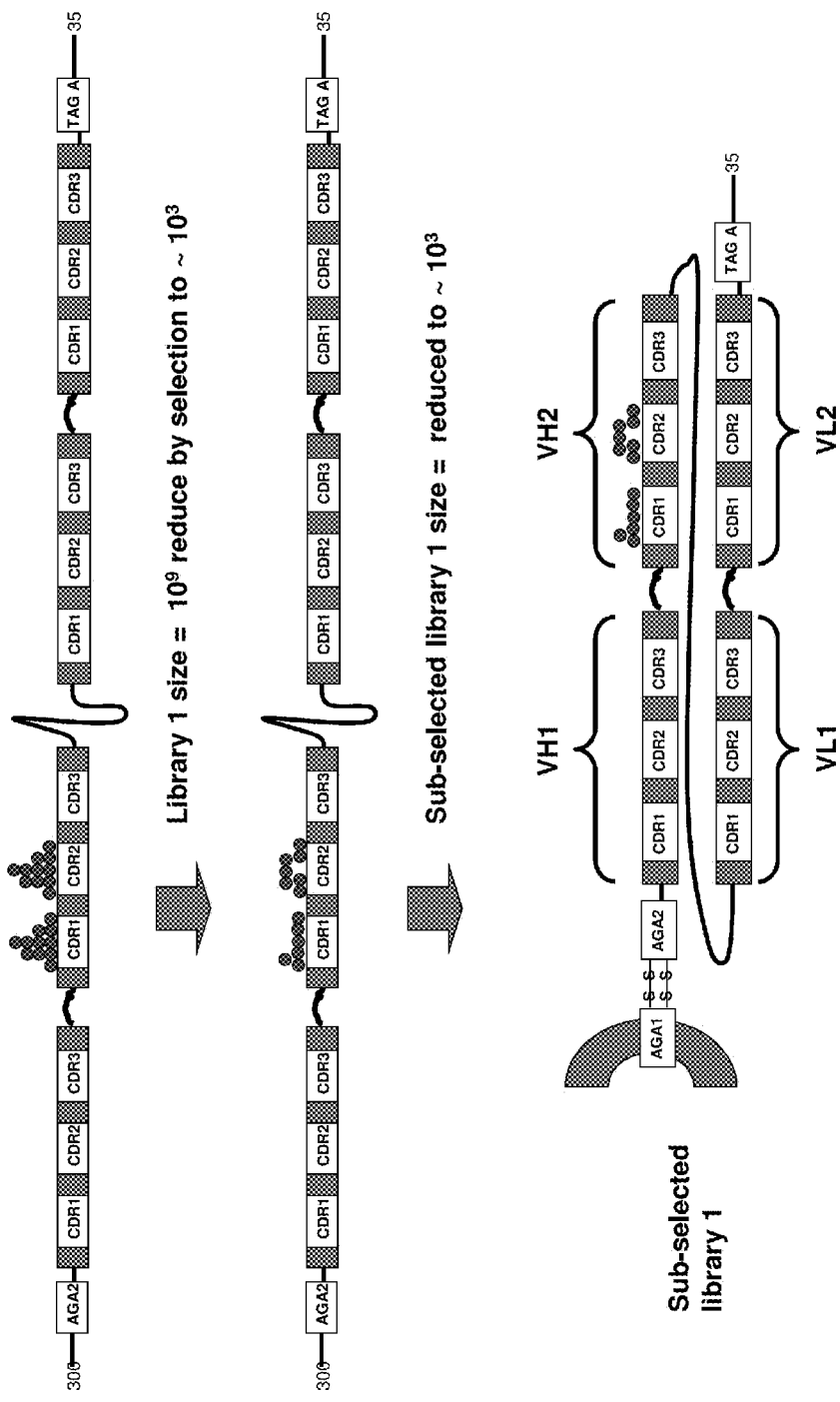

STEP 3D – display Library 4 clones on surface of yeast and select for binding to target antigen and TAG D

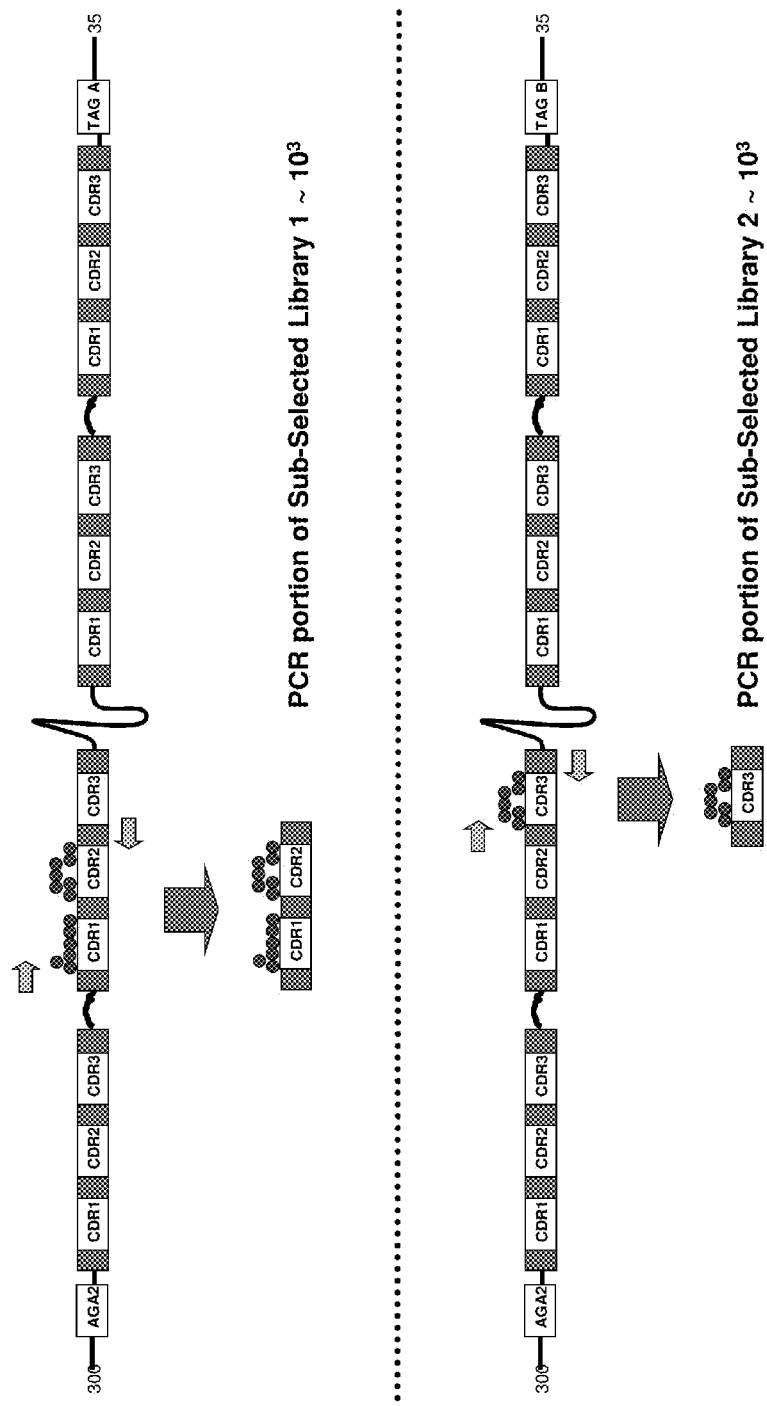

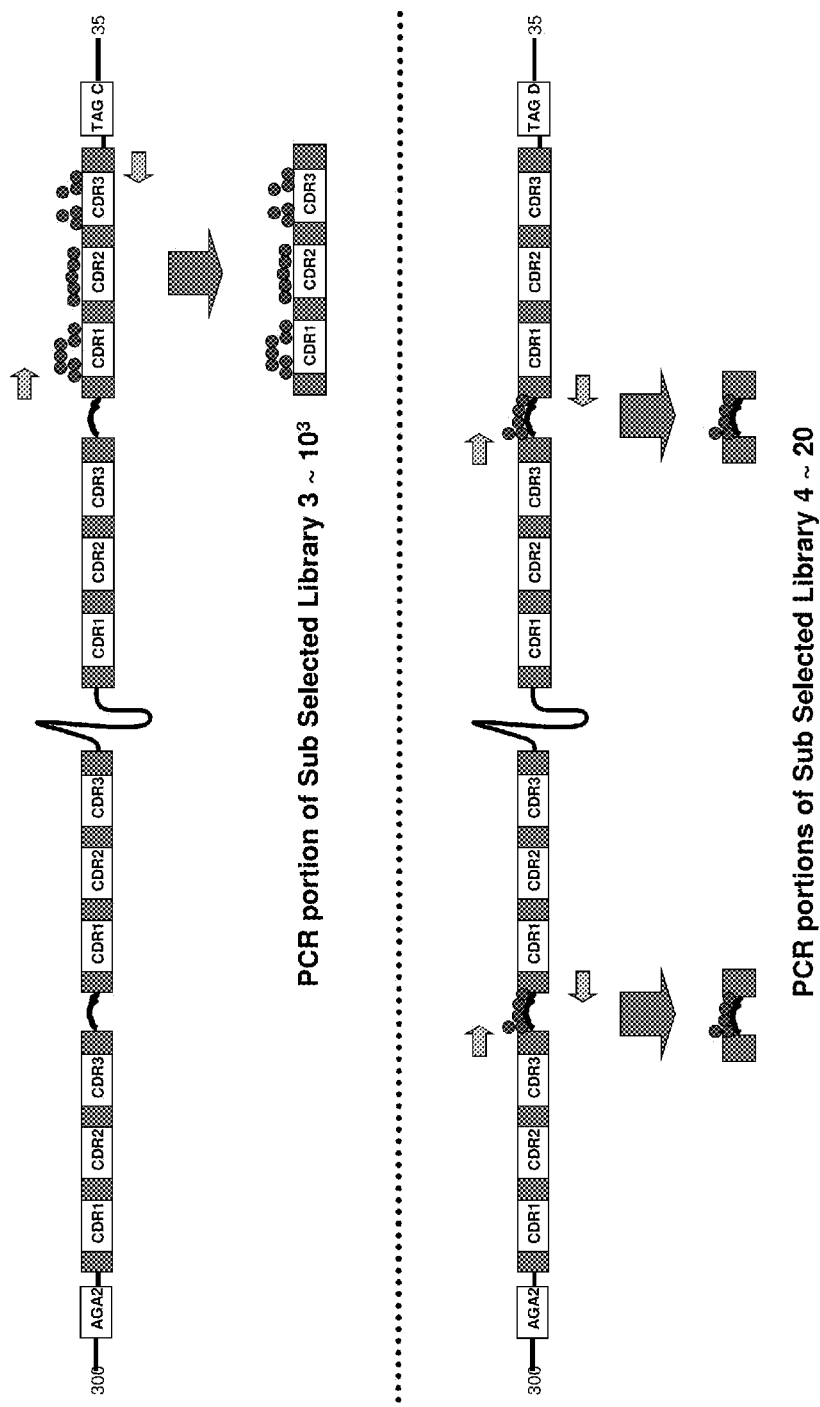

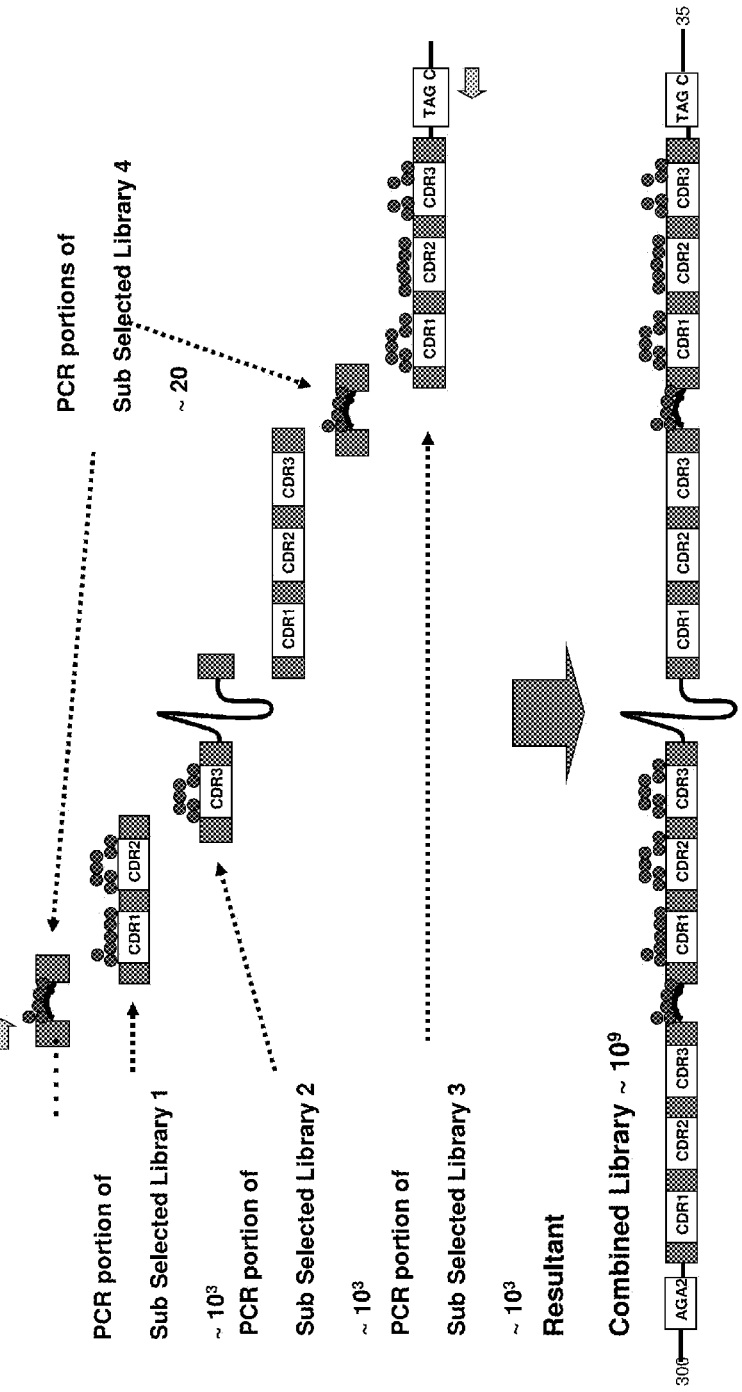

STEP 6 – linearized yeast vector, electroporate vector recombined library, yeast circularizes library by homologous recombination, propagate yeast so each becomes a clone expressing one sequence

Figure 11

A. Linear sequence cartoon of a scDVDFab

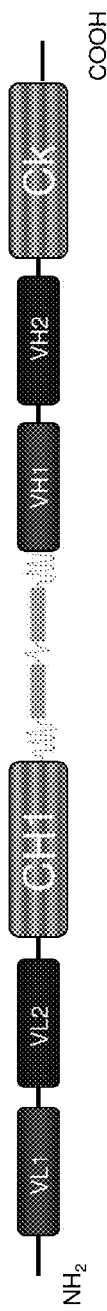

B. GS-rigid linker sequences

```
41 GS-rigid linker: GGGSGGGTPAPLPAPLPAPTGGGSGGG
49 GS-rigid linker: GGGSGGGTPAPLPAPLPAPLPAPTGGGSGGG
57 GS-rigid linker: GGGSGGGTPAPLPAPLPAPLPAPLPAPLPAPTGGGSGGG
65 GS-rigid linker: GGGSGGGTPAPLPAPLPAPLPAPLPAPLPAPLPAPTGGGSGGG
```

C. Linear sequence cartoon of a GS-rigid linker

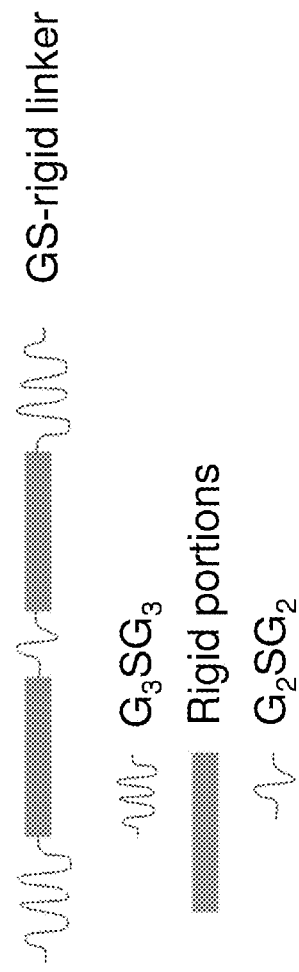

GS-rigid linker $G_3SG_3$

Rigid portions $G_2SG_2$

```
                        SEQUENCE LISTING

<160> NUMBER OF SEQ ID NOS: 101

<210> SEQ ID NO 1
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Gly Gly Ser Gly Gly Gly Thr Pro Leu Pro Ala Pro Leu Pro Ala
1               5                   10                  15

Pro Thr Gly Gly Ser Gly Gly Thr Pro Ala Pro Leu Pro Ala Pro Leu
            20                  25                  30

Pro Thr Gly Gly Gly Ser Gly Gly Gly
        35                  40

<210> SEQ ID NO 2
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Gly Gly Ser Gly Gly Gly Thr Pro Leu Pro Thr Pro Leu Pro Ala
1               5                   10                  15

Pro Leu Pro Ala Pro Thr Gly Gly Ser Gly Gly Thr Pro Ala Pro Thr
            20                  25                  30

Pro Ala Pro Leu Pro Ala Pro Leu Pro Thr Gly Gly Gly Ser Gly Gly
        35                  40                  45

Gly

<210> SEQ ID NO 3
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Gly Gly Ser Gly Gly Gly Thr Pro Leu Pro Ala Pro Leu Pro Thr
1               5                   10                  15

Pro Leu Pro Ala Pro Leu Pro Ala Pro Thr Gly Gly Ser Gly Gly Thr
            20                  25                  30

Pro Ala Pro Thr Pro Ala Pro Thr Pro Ala Pro Leu Pro Ala Pro Leu
        35                  40                  45

Pro Thr Gly Gly Gly Ser Gly Gly Gly
    50                  55
```

-continued

<210> SEQ ID NO 4
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Gly Gly Ser Gly Gly Gly Thr Pro Leu Pro Ala Pro Leu Pro Ala
1               5                   10                  15

Pro Leu Pro Thr Pro Leu Pro Ala Pro Leu Pro Ala Pro Thr Gly Gly
            20                  25                  30

Ser Gly Gly Thr Pro Ala Pro Thr Pro Ala Pro Thr Pro Ala Pro Thr
        35                  40                  45

Pro Ala Pro Leu Pro Ala Pro Leu Pro Thr Gly Gly Gly Ser Gly Gly
    50                  55                  60

Gly
65

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Pro Leu Pro Ala Pro Leu Pro Ala Pro Thr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Pro Leu Pro Thr Pro Leu Pro Ala Pro Leu Pro Ala Pro Thr
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Pro Leu Pro Ala Pro Leu Pro Thr Pro Leu Pro Ala Pro Leu Pro
1               5                   10                  15

Ala Pro Thr

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 8

Thr Pro Leu Pro Ala Pro Leu Pro Ala Pro Leu Pro Thr Pro Leu Pro
1               5                   10                  15

Ala Pro Leu Pro Ala Pro Thr
            20

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Leu Val Thr Val Ser Ser Gly Gly Gly Gly Ser Gly Gly Gly Gly
1               5                   10                  15

Ser Gly Gly Gly Gly Glu Val Gln Leu Val Glu Ser Gly
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Leu Val Thr Val Ser Ser Gly Gly Gly Gly Ser Gly Gly Gly Gly
1               5                   10                  15

Ser Gly Gly Gly Glu Val Gln Leu Val Glu Ser Gly
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Leu Val Thr Val Ser Ser Gly Gly Gly Gly Ser Gly Gly Gly Gly
1               5                   10                  15

Ser Gly Gly Glu Val Gln Leu Val Glu Ser Gly
            20                  25

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Leu Val Thr Val Ser Ser Gly Gly Gly Gly Ser Gly Gly Gly Gly
1               5                   10                  15

Ser Gly Glu Val Gln Leu Val Glu Ser Gly
            20                  25

<210> SEQ ID NO 13
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Leu Val Thr Val Ser Ser Gly Gly Gly Gly Ser Gly Gly Gly Gly
1               5                   10                  15

Ser Glu Val Gln Leu Val Glu Ser Gly
            20                  25

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Leu Val Thr Val Ser Ser Gly Gly Gly Gly Ser Gly Gly Gly Gly
1               5                   10                  15

Glu Val Gln Leu Val Glu Ser Gly
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Leu Val Thr Val Ser Ser Gly Gly Gly Gly Ser Gly Gly Gly Glu
1               5                   10                  15

Val Gln Leu Val Glu Ser Gly
            20

<210> SEQ ID NO 16
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Leu Val Thr Val Ser Ser Gly Gly Gly Gly Ser Gly Gly Glu Val
1               5                   10                  15

Gln Leu Val Glu Ser Gly
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Leu Val Thr Val Ser Ser Gly Gly Gly Gly Ser Gly Glu Val Gln
1               5                   10                  15
```

```
Leu Val Glu Ser Gly
         20

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Leu Val Thr Val Ser Ser Ala Ser Thr Lys Gly Pro Ser Val Phe
1               5                   10                  15

Pro Leu Ala Pro Glu Val Gln Leu Val Glu Ser Gly
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Leu Val Thr Val Ser Ser Ala Ser Thr Lys Gly Pro Ser Val Phe
1               5                   10                  15

Pro Leu Ala Glu Val Gln Leu Val Glu Ser Gly
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Leu Val Thr Val Ser Ser Ala Ser Thr Lys Gly Pro Ser Val Phe
1               5                   10                  15

Pro Leu Glu Val Gln Leu Val Glu Ser Gly
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Leu Val Thr Val Ser Ser Ala Ser Thr Lys Gly Pro Ser Val Phe
1               5                   10                  15

Pro Glu Val Gln Leu Val Glu Ser Gly
            20                  25

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 22

Thr Leu Val Thr Val Ser Ser Ala Ser Thr Lys Gly Pro Ser Val Phe
1               5                   10                  15

Glu Val Gln Leu Val Glu Ser Gly
            20

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Leu Val Thr Val Ser Ser Ala Ser Thr Lys Gly Pro Ser Val Glu
1               5                   10                  15

Val Gln Leu Val Glu Ser Gly
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Leu Val Thr Val Ser Ser Ala Ser Thr Lys Gly Pro Ser Glu Val
1               5                   10                  15

Gln Leu Val Glu Ser Gly
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Leu Val Thr Val Ser Ser Ala Ser Thr Lys Gly Pro Glu Val Gln
1               5                   10                  15

Leu Val Glu Ser Gly
            20

<210> SEQ ID NO 26
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Leu Val Thr Val Ser Ser Thr Pro Ala Pro Leu Pro Ala Pro Leu
1               5                   10                  15

Pro Ala Pro Thr Thr Glu Val Gln Leu Val Glu Ser Gly
            20                  25

<210> SEQ ID NO 27

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Leu Val Thr Val Ser Ser Thr Pro Ala Pro Leu Pro Ala Pro Ala
1               5                   10                  15

Pro Thr Thr Glu Val Gln Leu Val Glu Ser Gly
            20                  25

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Leu Val Thr Val Ser Ser Thr Pro Ala Pro Leu Pro Ala Pro Thr
1               5                   10                  15

Thr Glu Val Gln Leu Val Glu Ser Gly
            20                  25

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Leu Val Thr Val Ser Ser Thr Pro Ala Pro Leu Pro Thr Thr Glu
1               5                   10                  15

Val Gln Leu Val Glu Ser Gly
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Leu Val Thr Val Ser Ser Thr Pro Ala Pro Thr Thr Glu Val Gln
1               5                   10                  15

Leu Val Glu Ser Gly
            20

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Thr Lys Leu Glu Ile Lys Arg Gly Gly Ser Gly Gly Gly Gly Ser
1               5                   10                  15
```

Gly Gly Gly Gly Ser Asp Ile Gln Met Thr Gln Ser Pro
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Thr Lys Leu Glu Ile Lys Arg Gly Gly Ser Gly Gly Gly Gly Ser
1               5                   10                  15

Gly Gly Gly Gly Asp Ile Gln Met Thr Gln Ser Pro
            20                  25

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Thr Lys Leu Glu Ile Lys Arg Gly Gly Ser Gly Gly Gly Gly Ser
1               5                   10                  15

Gly Gly Gly Asp Ile Gln Met Thr Gln Ser Pro
            20                  25

<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Thr Lys Leu Glu Ile Lys Arg Gly Gly Ser Gly Gly Gly Gly Ser
1               5                   10                  15

Gly Gly Asp Ile Gln Met Thr Gln Ser Pro
            20                  25

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Thr Lys Leu Glu Ile Lys Arg Gly Gly Ser Gly Gly Gly Gly Ser
1               5                   10                  15

Gly Asp Ile Gln Met Thr Gln Ser Pro
            20                  25

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Thr Lys Leu Glu Ile Lys Arg Gly Gly Ser Gly Gly Gly Gly Ser
1               5                   10                  15

Asp Ile Gln Met Thr Gln Ser Pro
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Thr Lys Leu Glu Ile Lys Arg Gly Gly Ser Gly Gly Gly Gly Asp
1               5                   10                  15

Ile Gln Met Thr Gln Ser Pro
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Thr Lys Leu Glu Ile Lys Arg Gly Gly Ser Gly Gly Gly Asp Ile
1               5                   10                  15

Gln Met Thr Gln Ser Pro
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Thr Lys Leu Glu Ile Lys Arg Gly Gly Ser Gly Gly Asp Ile Gln
1               5                   10                  15

Met Thr Gln Ser Pro
            20

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Thr Lys Leu Glu Ile Lys Arg Thr Val Ala Ala Pro Ser Val Phe
1               5                   10                  15

Ile Phe Pro Pro Asp Ile Gln Met Thr Gln Ser Pro
            20                  25

```
<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Thr Lys Leu Glu Ile Lys Arg Thr Val Ala Ala Pro Ser Val Phe
1               5                   10                  15

Ile Phe Pro Asp Ile Gln Met Thr Gln Ser Pro
            20                  25

<210> SEQ ID NO 42
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Thr Lys Leu Glu Ile Lys Arg Thr Val Ala Ala Pro Ser Val Phe
1               5                   10                  15

Ile Phe Asp Ile Gln Met Thr Gln Ser Pro
            20                  25

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Thr Lys Leu Glu Ile Lys Arg Thr Val Ala Ala Pro Ser Val Phe
1               5                   10                  15

Ile Asp Ile Gln Met Thr Gln Ser Pro
            20                  25

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Thr Lys Leu Glu Ile Lys Arg Thr Val Ala Ala Pro Ser Val Phe
1               5                   10                  15

Asp Ile Gln Met Thr Gln Ser Pro
            20

<210> SEQ ID NO 45
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Thr Lys Leu Glu Ile Lys Arg Thr Val Ala Ala Pro Ser Val Asp
```

```
1               5                   10                  15
Ile Gln Met Thr Gln Ser Pro
            20

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Thr Lys Leu Glu Ile Lys Arg Thr Val Ala Ala Pro Ser Asp Ile
1               5                   10                  15

Gln Met Thr Gln Ser Pro
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Thr Lys Leu Glu Ile Lys Arg Thr Val Ala Ala Pro Asp Ile Gln
1               5                   10                  15

Met Thr Gln Ser Pro
            20

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Thr Lys Leu Glu Ile Lys Arg Thr Pro Ala Pro Leu Pro Ala Pro
1               5                   10                  15

Leu Pro Ala Pro Thr Asp Ile Gln Met Thr Gln Ser Pro
            20                  25

<210> SEQ ID NO 49
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Thr Lys Leu Glu Ile Lys Arg Thr Pro Ala Pro Leu Pro Ala Pro
1               5                   10                  15

Ala Pro Thr Asp Ile Gln Met Thr Gln Ser Pro
            20                  25

<210> SEQ ID NO 50
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 50

Gly Thr Lys Leu Glu Ile Lys Arg Thr Pro Ala Pro Leu Pro Ala Pro
1               5                   10                  15

Thr Asp Ile Gln Met Thr Gln Ser Pro
            20                  25

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Thr Lys Leu Glu Ile Lys Arg Thr Pro Ala Pro Leu Pro Thr Asp
1               5                   10                  15

Ile Gln Met Thr Gln Ser Pro
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Thr Lys Leu Glu Ile Lys Arg Thr Pro Ala Pro Thr Asp Ile Gln
1               5                   10                  15

Met Thr Gln Ser Pro
            20

<210> SEQ ID NO 53
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1-10 'Gly Gly Gly
      Gly Ser' repeating units, wherein some positions may be absent

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 54
<211> LENGTH: 5
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 54

Gly Gly Gly Gly Ser
1               5

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 55

Ala Ser Thr Lys Gly Pro Ser Val Phe Pro Leu Ala Pro Ser
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 56

Arg Thr Val Ala Ala Pro Ser Val Phe Ile Phe Pro Pro Ser
1               5                   10

<210> SEQ ID NO 57
<211> LENGTH: 508
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Tyr
            20                  25                  30

Gly Ile Ile Trp Val Arg Gln Ala Pro Gly Gln Gly Leu Glu Trp Met
        35                  40                  45

Gly Trp Ile Asn Thr Tyr Thr Gly Lys Pro Thr Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Leu Phe Thr Thr Met Asp Val Thr Asp Asn Ala Met Asp
            100                 105                 110

Tyr Trp Gly Gln Gly Thr Thr Val Thr Val Ser Ser Ala Ser Thr Lys
        115                 120                 125

Gly Pro Glu Val Gln Leu Val Glu Ser Gly Gly Leu Val Gln Pro
    130                 135                 140

Gly Arg Ser Leu Arg Leu Ser Cys Ala Ala Ser Gly Phe Thr Phe Asp
145                 150                 155                 160

Asp Tyr Ala Leu His Trp Val Arg Gln Ala Pro Gly Lys Gly Leu Glu
                165                 170                 175

Trp Val Ser Gly Ile Ser Trp His Gly Asp Phe Ile Asp Tyr Ala Asp
            180                 185                 190

Ser Val Lys Gly Arg Phe Thr Ile Ser Arg Asp Asn Ala Lys Asn Ser
            195                 200                 205

Leu Tyr Leu Gln Met Asn Ser Leu Arg Val Glu Asp Thr Ala Leu Tyr
            210                 215                 220

Tyr Cys Ala Gly Asn Asn Arg Gly Tyr Gly Gly Leu Asp Val Trp Gly
225                 230                 235                 240

Gln Gly Thr Thr Val Thr Val Ser Ser Gly Gly Gly Ser Gly Gly
            245                 250                 255

Gly Gly Ser Gly Gly Gly Gly Ser Gly Gly Gly Gly Ser Gly Gly Gly
            260                 265                 270

Gly Ser Gly Gly Gly Gly Ser Gly Gly Gly Gly Ser Asp Ile Gln Met
            275                 280                 285

Thr Gln Ser Pro Ser Ser Leu Ser Ala Ser Val Gly Asp Arg Val Thr
            290                 295                 300

Ile Thr Cys Arg Ala Ser Gln Asp Ile Ser Gln Tyr Leu Asn Trp Tyr
305                 310                 315                 320

Gln Gln Lys Pro Gly Lys Ala Pro Lys Leu Leu Ile Tyr Tyr Thr Ser
            325                 330                 335

Arg Leu Gln Ser Gly Val Pro Ser Arg Phe Ser Gly Ser Gly Ser Gly
            340                 345                 350

Thr Asp Phe Thr Leu Thr Ile Ser Ser Leu Gln Pro Glu Asp Phe Ala
            355                 360                 365

Thr Tyr Phe Cys Gln Gln Gly Asn Thr Trp Pro Thr Phe Gly Gln
            370                 375                 380

Gly Thr Lys Leu Glu Ile Lys Arg Thr Val Ala Ala Pro Gln Ser Val
385                 390                 395                 400

Leu Thr Gln Pro Pro Ser Ala Ser Gly Thr Pro Gly Gln Arg Val Thr
            405                 410                 415

Ile Ser Cys Ser Gly Ser Ser Ser Asn Ile Gly Ser Asn Thr Val Asn
            420                 425                 430

Trp Tyr Gln Gln Leu Pro Gly Thr Ala Pro Lys Leu Leu Ile Tyr Ser
            435                 440                 445

Asn Asn Gln Arg Pro Ser Gly Val Pro Asp Arg Phe Ser Gly Ser Lys
            450                 455                 460

Ser Gly Thr Ser Ala Ser Leu Ala Ile Ser Gly Leu Gln Ser Glu Asp
465                 470                 475                 480

Glu Ala Asp Tyr Tyr Cys Ala Ala Trp Asp Asp Ser Leu Asn Gly Ser
            485                 490                 495

Tyr Val Phe Gly Gly Gly Thr Lys Leu Thr Val Leu
            500                 505

<210> SEQ ID NO 58
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr

```
                   20                  25                  30
Ala Met His Trp Val Arg Gln Ala Pro Gly Lys Gly Leu Glu Trp Val
                35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Tyr Tyr Tyr Gly Met Asp Val Trp Gly Gln Gly
                100                 105                 110

Thr Thr Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Asp Asp Tyr
                20                  25                  30

Ala Leu His Trp Val Arg Gln Ala Pro Gly Lys Gly Leu Glu Trp Val
                35                  40                  45

Ser Gly Ile Ser Trp His Gly Asp Phe Ile Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Val Glu Asp Met Ala Ile Tyr Tyr Cys
                85                  90                  95

Ala Gly Asn Asn Arg Gly Tyr Gly Gly Leu Asp Val Trp Gly Gln Gly
                100                 105                 110

Thr Thr Val Thr Val Ser Ser
        115

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
```

```
                 65                  70                  75                  80
Ser Glu Asp Glu Ala Asp Tyr Tyr Cys Ala Ala Trp Asp Asp Ser Leu
                 85                  90                  95

Asn Gly Pro Val Val Phe Gly Gly Gly Thr Lys Leu Thr Val Leu
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Ser Gly Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Ser Tyr Val Phe Gly Gly Gly Thr Lys Leu Thr Val Leu
            100                 105                 110

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gly Thr Lys Leu Glu Ile Lys Arg Thr Val Ala Ala Pro Ser Val
1               5                   10                  15

Phe Ile Phe Pro Gln Ser Val Leu Thr Gln Pro Pro
            20                  25

<210> SEQ ID NO 63
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gly Thr Lys Leu Glu Ile Lys Arg Thr Val Ala Ala Pro Ser Val
1               5                   10                  15

Phe Ile Gln Ser Val Leu Thr Gln Pro Pro
            20                  25

<210> SEQ ID NO 64
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 64

Gln Gly Thr Lys Leu Glu Ile Lys Arg Thr Val Ala Ala Pro Ser Val
1               5                   10                  15

Gln Ser Val Leu Thr Gln Pro Pro
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gly Thr Lys Leu Glu Ile Lys Arg Thr Val Ala Ala Pro Gln Ser
1               5                   10                  15

Val Leu Thr Gln Pro Pro
            20

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Gly Thr Lys Leu Glu Ile Lys Arg Gly Gly Ser Gly Gly Gly Gly
1               5                   10                  15

Ser Gly Gly Gly Gln Ser Val Leu Thr Gln Pro Pro
            20                  25

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gly Thr Lys Leu Glu Ile Lys Arg Gly Gly Ser Gly Gly Gly Gly
1               5                   10                  15

Ser Gly Gln Ser Val Leu Thr Gln Pro Pro
            20                  25

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gly Thr Lys Leu Glu Ile Lys Arg Gly Gly Ser Gly Gly Gly Gly
1               5                   10                  15

Gln Ser Val Leu Thr Gln Pro Pro
            20
```

<210> SEQ ID NO 69
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gly Thr Lys Leu Glu Ile Lys Arg Gly Gly Ser Gly Gly Gln Ser
1               5                   10                  15

Val Leu Thr Gln Pro Pro
            20

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gly Thr Lys Leu Glu Ile Lys Arg Thr Pro Ala Pro Leu Pro Ala
1               5                   10                  15

Pro Ala Pro Thr Gln Ser Val Leu Thr Gln Pro Pro
            20                  25

<210> SEQ ID NO 71
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gly Thr Lys Leu Glu Ile Lys Arg Thr Pro Ala Pro Leu Pro Ala
1               5                   10                  15

Pro Thr Gln Ser Val Leu Thr Gln Pro Pro
            20                  25

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gly Thr Lys Leu Glu Ile Lys Arg Thr Pro Ala Pro Leu Pro Thr
1               5                   10                  15

Gln Ser Val Leu Thr Gln Pro Pro
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gly Thr Lys Leu Glu Ile Lys Arg Thr Pro Ala Pro Thr Gln Ser
1               5                   10                  15

Val Leu Thr Gln Pro Pro
            20

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
catcatcacc atcaccat                                                 18

<210> SEQ ID NO 75
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggtaagccta tccctaaccc tctcctcggt ctcgattcta cg                      42

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gaacaaaaac ttatttctga agaagatctg                                    30

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tacccatacg atgttccgga ttacgct                                       27

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agccagccag aactcgctcc tgaagaccca gaggac                             36

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
gactacaagg acgacgacga caag                                              24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tggagccatc cgcagtttga gaag                                              24

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tccagcacct cgagtgattt tcgagatcgc                                        30

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aaggaaaccg cggctgccaa gtttgaacgc cagcatatgg atagc                       45

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggagcgcctg taccatatcc ggatccgctg gaaccgcgc                              39

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
agctggaagg atgcgagcgg ctggagc                                           27

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 85

His His His His His His
1               5

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Lys Pro Ile Pro Asn Pro Leu Leu Gly Leu Asp Ser Thr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Gln Lys Leu Ile Ser Glu Glu Asp Leu
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Pro Tyr Asp Val Pro Asp Tyr Ala
1               5

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Gln Pro Glu Leu Ala Pro Glu Asp Pro Glu Asp
1               5                   10

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Tyr Lys Asp Asp Asp Asp Lys
1               5

<210> SEQ ID NO 91
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Ser His Pro Gln Phe Glu Lys
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ser Thr Ser Ser Asp Phe Arg Asp Arg
1               5                   10

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Glu Thr Ala Ala Ala Lys Phe Glu Arg Gln His Met Asp Ser
1               5                   10                  15

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ala Pro Val Pro Tyr Pro Asp Pro Leu Glu Pro Arg
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Trp Lys Asp Ala Ser Gly Trp Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Gly Ser Gly Gly Gly
```

```
<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Ser Gly Gly
1               5

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Pro Ala Pro Leu Pro Ala Pro Leu Pro Thr
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Pro Ala Pro Thr Pro Ala Pro Leu Pro Ala Pro Leu Pro Thr
1               5                   10                  15

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Pro Ala Pro Leu Pro Ala Pro Thr Pro Ala Pro Leu Pro Ala Pro
1               5                   10                  15

Leu Pro Thr

<210> SEQ ID NO 101
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Pro Ala Pro Leu Pro Ala Pro Leu Pro Ala Pro Thr Pro Ala Pro
1               5                   10                  15

Leu Pro Ala Pro Leu Pro Thr
            20
```

US 9,458,244 B2

SINGLE CHAIN MULTIVALENT BINDING PROTEIN COMPOSITIONS AND METHODS

RELATED APPLICATIONS

This application claims priority from U.S. Provisional Application No. 61/746,659, filed on Dec. 28, 2012, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 21, 2014, is named 553456(BBI-331)_SL.txt and is 41,457 bytes in size.

BACKGROUND

I. Field

The present disclosure pertains to methods and compositions for producing single chain multivalent binding proteins that specifically bind to one or more desired target antigens. More specifically, the disclosure relates to protein, nucleic acid, and cellular libraries of single chain multivalent binding proteins (e.g., scDVD molecules) and methods of using these libraries for the screening of single chain multivalent binding proteins using cell surface display technology (e.g., yeast display).

II. Description of Related Art

A wide variety of multispecific antibody formats have been developed (see Kriangkum, J., et al., Biomol Eng, 2001. 18(2): p. 31-40). Amongst them tandem single-chain Fv molecules and diabodies, and various derivatives there of, are the most widely used formats for the construction of recombinant bispecific antibodies. More recently diabodies have been fused to Fc to generate more Ig-like molecules, named di-diabodies (see Lu, D., et al., J Biol Chem, 2004. 279(4): p. 2856-65). In addition, multivalent antibody construct comprising two Fab repeats in the heavy chain of an IgG and capable of binding four antigen molecules has been described (see WO 0177342A1, and Miller, K., et al., J Immunol, 2003. 170(9): p. 4854-61).

Despite the many bispecific antibody formats available to the skilled artisan, there is often a need for the skilled artisan to improve the affinity of the bispecific antibody through affinity maturation. However, conventional affinity maturation approaches rely upon screening for affinity matured variants of the component binding domains of the multispecific antibody followed by their reassembly into the original multispecific format. Such reassembly often results in a loss of the desired improvement in binding affinity or other desirable binding characteristics. Accordingly, there is a need in the art for improved constructs, formats, and screening methodologies for identifying affinity variants of multivalent binding proteins in their desired multivalent format.

SUMMARY

The present disclosure provides a novel compositions and methods useful for the generation of improved single-chain multivalent binding proteins (e.g., scDVD) capable of binding two or more antigens simultaneously with high affinity.

Accordingly, in one aspect, the disclosure provides a single chain multivalent binding protein.

In certain embodiments, the single chain multivalent binding protein has the general formula VH1-(X1)n-VH2-X2-VL1-(X3)n-VL2, wherein VH1 is a first antibody heavy chain variable domain, X1 is a linker with the proviso that it is not a constant domain, VH2 is a second antibody heavy chain variable domain, X2 is a linker, VL1 is a first antibody light chain variable domain, X3 is a linker with the proviso that it is not a constant domain, VL2 is a second antibody light chain variable domain, and n is 0 or 1, and wherein the VH1 and VL1, and the VH2 and VL2 respectively combine to form two functional antigen binding sites.

In certain embodiments, the single chain binding protein has the formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain heavy domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, and the VH2 and VL2 respectively combine to form two functional antigen binding sites. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, the single chain multivalent binding protein has the general formula (VL1-(X1)n-VL2-X2-VH1-(X3)n-VH2, wherein VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VH2 is a second antibody heavy chain variable domain, and n is 0 or 1, and wherein the VH1 and VL1, and the VH2 and VL2 respectively combine to form two functional antigen binding site.

In certain embodiments, the single chain binding protein has the formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, and the VH2 and VL2 respectively combine to form two functional antigen binding site. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, the single chain multivalent binding protein is a single-chain dual variable domain immunoglobulin molecules (scDVD).

In certain embodiments, the single chain multivalent binding protein further comprising a cell surface anchoring moiety linked to the N and/or C terminus. In one embodiment, the anchoring moiety comprises the Aga2p polypeptide.

In another aspect, the disclosure provides a polynucleotide encoding a binding protein disclosed herein.

In another aspect, the disclosure provides a host cell expressing a binding protein disclosed herein.

In another aspect, the disclosure provides a diverse library of binding proteins. In certain embodiments, the diverse library of binding proteins comprises a polypeptide chain having the general formula VH1-(X1)n-VH2-X2-VL1-(X3)n-VL2, wherein VH1 is a first heavy chain variable domain, X1 is a linker with the proviso that it is not a constant domain, VH2 is a second heavy chain variable domain, X2 is a linker, VL1 is a first light chain variable domain, X3 is a linker with the proviso that it is not a constant domain, VL2 is a second light chain variable domain, and n is 0 or 1, wherein the VH1 and VL1, and the VH2 and VL2 respectively combine to form two functional antigen binding sites, and wherein the amino acid sequences of VH1, X1, VH2, X2, VL1, X3, and/or VL2 independently vary within the library.

In certain embodiments, the diverse library of binding proteins comprises a polypeptide chain having the general formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain constant domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, the VH2 and VL2 respectively combine to form two functional antigen binding sites, and wherein the amino acid sequences of VH1, X1, VH2, X2, VL1, X3, and/or VL2 independently vary within the library. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, the diverse library of binding proteins comprises a polypeptide chain having the general formula (VL1-(X1)n-VL2-X2-VH1-(X3)n-VH2, wherein VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VH2 is a second antibody heavy chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library.

In certain embodiments, the diverse library of binding proteins comprises a polypeptide chain having the general formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, the VH2 and VL2 respectively combine to form two functional antigen binding site, and wherein the amino acid sequences of VH1, X1, VH2, X2, VL1, X3, and/or VL2 independently vary within the library. In certain embodiments, the CL1 light chain. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, each binding proteins further comprises a cell surface anchoring moiety linked to the N or C terminus. In certain embodiments, the anchoring moiety is a cell surface protein. In one embodiment, the anchoring moiety is Aga2p.

In certain embodiments, the polypeptide chain is a scDVD or scDVDFab.

In certain embodiments, the amino acid sequence of at least one CDR of VH1, VH2, VL1 or VL2 independently varies within the library. In one embodiment, the amino acid sequence of HCDR3 of VH1, VH2 independently vary within the library. In one embodiment, the amino acid sequence of HCDR1 and HCDR2 of VH1 or VH2 independently vary within the library. In one embodiment, the amino acid sequence of HCDR1, HCDR2 and HCDR3 of VH1 or VH2 independently vary within the library. In one embodiment, the amino acid sequence of HCDR3 of VL1 or VL2 independently vary within the library. In one embodiment, the amino acid sequence of HCDR1 and HCDR2 of VL1 or VL2 independently vary within the library. In one embodiment, the amino acid sequence of HCDR1, HCDR2 and HCDR3 of VL1 or VL2 independently vary within the library.

In certain embodiments, X1 independently varies within the library and wherein X1 is selected from the amino acid sequences set forth in FIG. 2. In certain embodiments, X2 independently varies within the library and wherein X2 is $(G_4S)n$, where n=1-10(SEQ ID NO: 53). In other embodiments, X2 is selected from the amino acid sequences set forth in FIG. 11B. In specific embodiments, X2 is selected from the amino acid sequences set forth in FIG. 11B when the polypeptide chain includes CH and CL domain. In certain embodiments, X3 independently varies within the library and X3 is selected from the amino acid sequences set forth in FIG. 2.

In certain embodiments, the library of binding proteins share at least 70, 75, 80, 85, 90, 95, 96, 97, 98, or 99 amino acid sequence identity with a reference binding protein. In certain embodiments, VH1 and VH2 of the reference binding protein specifically bind to different antigens.

In another aspect, the disclosure provides a diverse library of polynucleotides encoding a diverse library of binding proteins disclosed herein.

In another aspect, the disclosure provides a diverse library of expression vectors comprising a diverse library of polynucleotides disclosed herein.

In another aspect, the disclosure provides a library of transformed host cells, expressing the diverse library of binding proteins disclosed herein.

In certain embodiments, the binding proteins are anchored on the cell surface of a transformed host cell. In certain embodiments, the binding proteins are anchored on the cell surface through Aga1p.

In certain embodiments, the host cells are eukaryotic. In certain embodiments, the host cells are yeast, e.g., *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula* rubra, *Schizosaccharomyces pombe* and *Yarrowia lipolytica*. In one embodiment, the yeast is *Saccharomyces cerevisiae*.

In another aspect, the disclosure provides a method of selecting a binding protein that specifically binds to a target antigen, the method comprising: providing a diverse library of transformed host cells expressing a diverse library of binding proteins disclosed herein; contacting the host cells with the target antigen; and selecting a host cell that bind to the target antigen, thereby identifying a binding protein that specifically binds to a target antigen.

In another aspect, the disclosure provides a method of selecting a binding protein that specifically binds to a first and a second target antigen simultaneously, the method comprising: providing a diverse library of transformed host cells expressing a diverse library of binding proteins disclosed herein; contacting the host cells with the first and second target antigen; and selecting a host cell that bind to the first and second target antigen, thereby identifying a binding protein that specifically binds to a first and a second target antigen simultaneously.

In certain embodiments of the methods disclosed herein, host cells that bind to the first and/or second antigen are selected by Magnetic Activated Cell Sorting using magnetically labeled antigen. In certain embodiments of the methods disclosed herein, host cells that bind to the first and/or second antigen are selected by Fluorescence Activated Cell Sorting using fluorescently labeled antigen.

In certain embodiments, the methods disclosed herein further comprise isolating the binding protein-encoding polynucleotide sequences from the selected host cells.

In another aspect, the disclosure provides a method of producing a binding protein comprising expressing in a host cell a binding protein that was selected using the methods disclosed herein.

In another aspect, the disclosure provides method of producing a diverse library of binding proteins that specifically binds to a target antigen, the method comprising: providing a first diverse library of scDVD or scDVDFab molecules, wherein the amino acid sequence of a first region of the scDVD or scDVDFab molecules is varied in the library, and wherein each member of the library binds to the target antigen; providing a second diverse library of scDVD or scDVDFab molecules, wherein the amino acid sequence of a second region of the scDVD or scDVDFab molecules is varied in the library, and wherein each member of the library binds to the target antigen; recombining the first and second libraries to produce a third diverse library of scDVD or scDVDFab molecules, wherein the third library comprises the first regions from the first library and the second region from the second library, thereby producing a diverse library of binding proteins that specifically binds to a target antigen.

In certain embodiments, the first and second libraries are recombined by yeast gap repair of polynucleotides encoding the libraries.

BRIEF DESCRIPTION OF THE DRAWINGS

FIG. 2 discloses "(G₄S)ₙ," as SEQ ID NO:54.

FIG. 11 depicts (A) a schematic representation of an scDVDFab molecule, (B) GS-rigid linker amino acid sequences (SEQ ID NOs:1-4) and (C) a schematic of a scDVDFab with a GS-rigid linker (FIG. 11C discloses "G₃SG₃" as SEQ ID NO:96 and "G₂SG₂" as SEQ ID NO:97).

DETAILED DESCRIPTION

The present disclosure provides a novel compositions and methods useful for the generation of improved single-chain multivalent binding proteins (e.g., scDVD) capable of binding two or more antigens simultaneously with high affinity.

I. Definitions

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

In order that the disclosure may be more readily understood, certain terms are first defined.

The term "multivalent binding protein" is used throughout this specification to denote a binding protein comprising two or more antigen binding sites, each of which can bind independently bind to an antigen.

The terms "dual variable domain immunoglobulin" or "DVD-Ig" refer to the multivalent binding proteins disclosed in, e.g., U.S. Pat. No. 8,258,268, which is herein incorporated by reference in its entirety.

Figure 1:
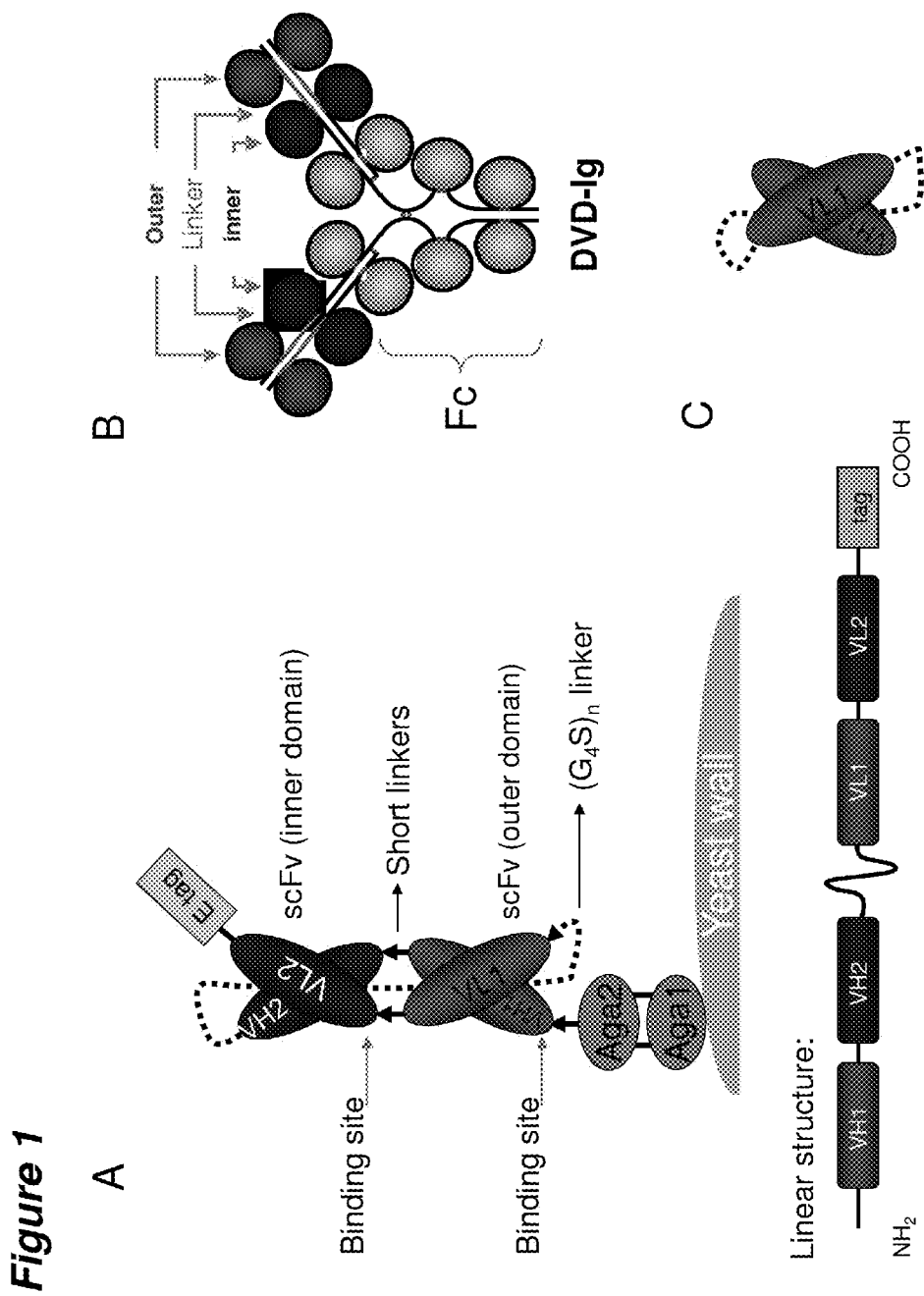
FIG. 1 depicts (A) an exemplary single chain dual variable domain (scDVD) molecules (FIG. 1A discloses "(G₄S)ₙ" as SEQ ID NO:54), (B) an exemplary full-length DVD-Ig molecule, and (C) an exemplary a single chain Fv molecule.

The terms "single chain dual variable domain immunoglobulin" or "scDVD" refer to the antigen binding fragment of a DVD molecule that is analogous to an antibody single chain Fv fragment. scDVD are generally of the formula VH1-(X1)n-VH2-X2-VL1-(X3)n-VL2, where VH1 is a first antibody heavy chain variable domain, X1 is a linker with the proviso that it is not a constant domain, VH2 is a second antibody heavy chain variable domain, X2 is a linker, VL1 is a first antibody light chain variable domain, X3 is a linker with the proviso that it is not a constant domain, VL2 is a second antibody light chain variable domain, and n is 0 or 1, where the VH1 and VL1, and the VH2 and VL2 respectively combine to form two functional antigen binding sites. An exemplary scDVD is depicted in FIG. 1 herein.

The terms "single chain dual variable domain immunoglobulin Fab" or "scDVDFab" refer to the antigen binding fragment of a DVD molecule that includes the variable heavy (VH) and light (VL) chains of a DVD-Ig. scDVD are generally of the formula CH1-X0-VH1-(X1)n-VH2-X2-CL1-X4-VL1-(X3)n-VL2, where CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain constant domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, where the VH1 and VL1, and the VH2 and VL2 respectively combine to form two functional antigen binding sites. Optionally, the CL1 domain can be a kappa (hcκ or cκ) or a lambda (hcλ or cλ) constant domain. In certain embodiments, CL1 is cκ. An exemplary scDVDFab is depicted in FIG. 10A, herein.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al. Nature; 264: 415-20; Thies et al 1999 J Mol Biol; 293: 67-79.). Mutation of cysteine residues within the hinge regions to prevent heavy chain-heavy chain disulfide bonds will destabilize dimeration of CH3 domains. Residues responsible for CH3 dimerization have been identified (Dall'Acqua 1998 Biochemistry 37: 9266-73.). Therefore, it is possible to generate a monovalent half-Ig. Interestingly, these monovalent half Ig molecules have been found in nature for both IgG and IgA subclasses (Seligman 1978 Ann Immunol 129: 855-70; Biewenga et al 1983 Clin Exp Immunol 51: 395-400). The stoichiometry of FcRn: Ig Fc region has been determined to be 2:1 (West et al 2000 Biochemistry 39: 9698-708), and half Fc is sufficient for mediating FcRn binding (Kim et al 1994 Eur J Immunol; 24: 542-548.). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However the half Ig molecule may have certain advantage in tissue penetration due to its smaller size than that of a regular antibody. In one embodiment at least one amino acid residue is replaced in the constant region of the binding protein disclosed herein, for example the Fc region, such that the dimerization of the heavy chains is disrupted, resulting in half DVD Ig molecules.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the terms "CH1 domain" and "CL1 domain" refer to single antibody heavy and light constant regions. A CL1 domain can be a Cκ or a Cλ domain.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

As used herein the term "framework (FR) amino acid residues" refers to those amino acids in the framework region of an immunogobulin chain. The term "framework region" or "FR region" as used herein, includes the amino acid residues that are part of the variable region, but are not part of the CDRs (e.g., using the Kabat definition of CDRs).

As used herein, the term "specifically binds to" refers to the ability of a binding polypeptide to bind to an antigen with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or bind to an antigen with an affinity that is at least two-fold greater than its affinity for a nonspecific antigen. It shall be understood, however, that the binding polypeptide are capable of specifically binding to two or more antigens which are related in sequence. For example, the binding polypeptides disclosed herein can specifically bind to both human and a non-human (e.g., mouse or non-human primate) orthologs of an antigen.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "linker" is used to denote polypeptides comprising two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). Preferred linkers include, but are not limited to, the amino acid linkers set forth in Table 7 herein.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "Kd", as used herein, is intended to refer to the dissociation constant of a particular antibody-antigen interaction as is known in the art.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

II. Single-chain Multivalent Binding Proteins

In one aspect, the disclosure provides single-chain multivalent binding proteins that can bind to two antigen simultaneously. In certain embodiments, the single-chain multivalent binding proteins generally comprise a polypeptide of the formula VH1-(X1)n-VH2-X2-VL1-(X3)n-VL2, where VH1 is a first antibody heavy chain variable domain, X1 is a linker with the proviso that it is not a constant domain, VH2 is a second antibody heavy chain variable domain, X2 is a linker, VL1 is a first antibody light chain variable domain, X3 is a linker with the proviso that it is not a constant domain, VL2 is a second antibody light chain variable domain, and n is 0 or 1, where the VH1 and VL1, and the VH2 and VL2 respectively combine to form two functional antigen binding sites.

In certain embodiments, the single chain binding protein has the formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain heavy domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, and the VH2 and VL2 respectively combine to form two functional antigen binding sites. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, the single-chain multivalent binding proteins generally comprise a polypeptide of the formula VL1-(X1)n-VL2-X2-VH1-(X3)n-VH2, where VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VHL2 is a second antibody heavy chain variable domain, and n is 0 or 1, where the VH1 and VL1, and the VH2 and VL2 respectively combine to form two functional antigen binding sites In certain embodiments, the single chain binding protein has the formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, and the VH2 and VL2 respectively combine to form two functional antigen binding site. Optionally, the CL1 domain can be a kappa (hcκ or cκ) or a lambda (hcλ or cλ) constant domain. In certain embodiments, CL1 is cκ.

In certain embodiments, X2 is a GS-rigid linker sequence. The GS rigid linker sequence can comprise an amino acid sequence selected from the group consisting of SEQ ID NOs:1-4.

In certain embodiments, the single-chain multivalent binding proteins are single-chain dual variable domain immunoglobulin molecules (scDVD). An exemplary scDVD is depicted in FIG. 1 herein. In other embodiments, the single-chain multivalent binding proteins are single-chain dual variable domain immunoglobulin Fab molecules (scDVDFab). An exemplary scDVDFab is depicted in FIG. 10A, herein.

In certain embodiments, the multivalent binding proteins comprise a cell surface anchoring moiety linked to the N and/or C terminus. Any molecule that can display the binding protein on the surface of a cell can be employed including, without limitation, cell surface protein and lipids. In certain embodiments, the anchoring moiety comprises the Aga2p polypeptide.

The antibody variable domains for the use in the single-chain multivalent binding proteins disclosed herein can be obtained using recombinant DNA techniques from a parent antibody (or DVD-Ig) generated by any method known in the art. In a certain embodiments, the variable domain is a murine heavy or light chain variable domain. In a certain embodiments, the variable domain is a CDR grafted or a humanized variable heavy or light chain domain. In a certain embodiments, the variable domain is a human heavy or light chain variable domain.

In certain embodiments, the first and second variable domains are linked directly to each other using recombinant DNA techniques. In certain embodiments, the variable domains are linked via a linker sequence. Preferably two variable domains are linked. Three or more variable domains may also be linked directly or via a linker sequence. The variable domains may bind the same antigen or may bind different antigens. Single-chain multivalent binding proteins molecules disclosed herein may include one immunoglobulin variable domain and one non-immunoglobulin variable domain such as ligand binding domain of a receptor, active domain of an enzyme. Single-chain multivalent binding proteins molecules may also comprise two or more non-Ig domains.

The linker sequence may be a single amino acid or a polypeptide sequence. Preferably the linker sequences are selected from the group consisting of consisting of the amino acid sequences set forth in FIG. 2 herein.

In certain embodiments, a heavy chain or light chain constant domain is linked to the single-chain multivalent binding proteins domains using recombinant DNA techniques. Additionally or alternatively, in certain embodiments, the DVD heavy chain is linked to an Fc region. The Fc region may be a native sequence Fc region, or a variant Fc region. In certain embodiments, the Fc region is a human Fc region. In one embodiment the Fc region includes an Fc region from IgG1, IgG2, IgG3, IgG4, IgA, IgM, IgE, or IgD.

III. Libraries of Multivalent Binding Protein

Figure 8:
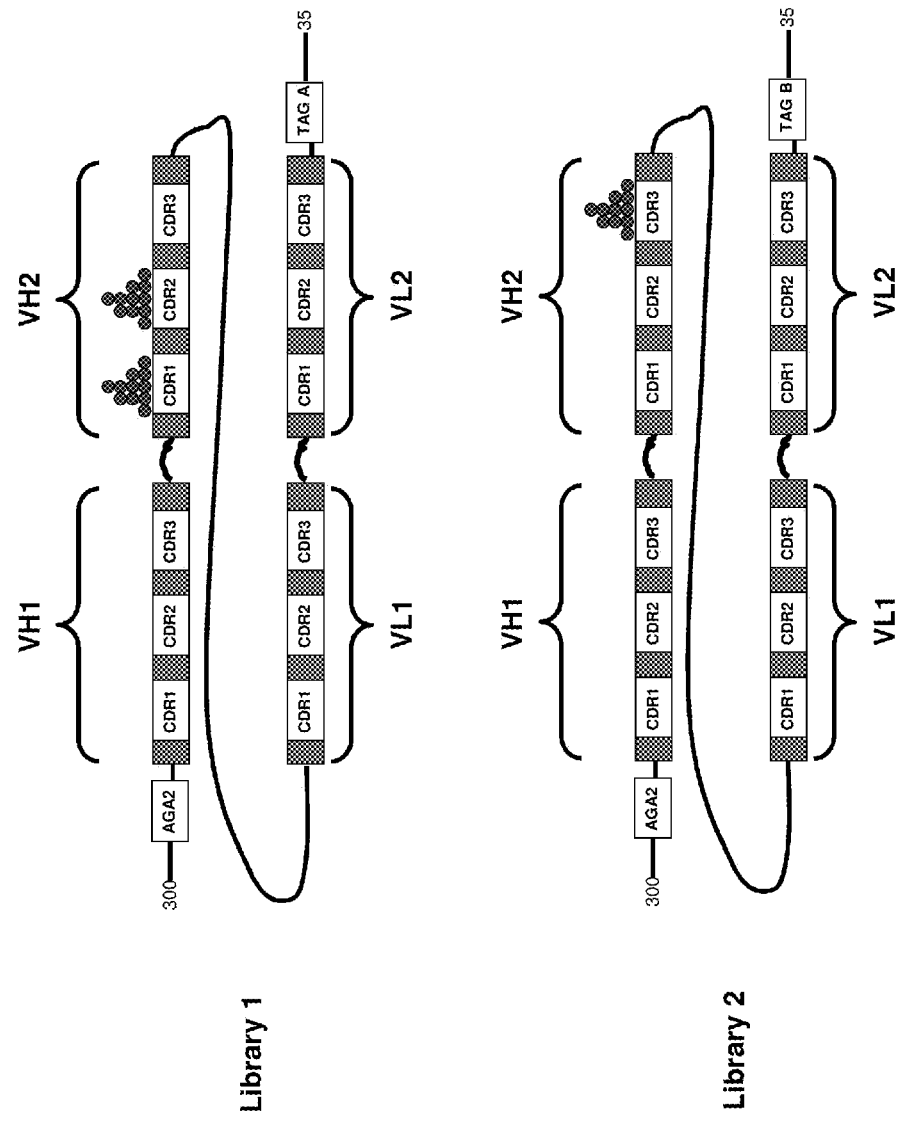
FIG. 8 is a schematic representation of exemplary scDVD libraries disclosed herein and multiplexing methods of using these libraries.
Figure 8:
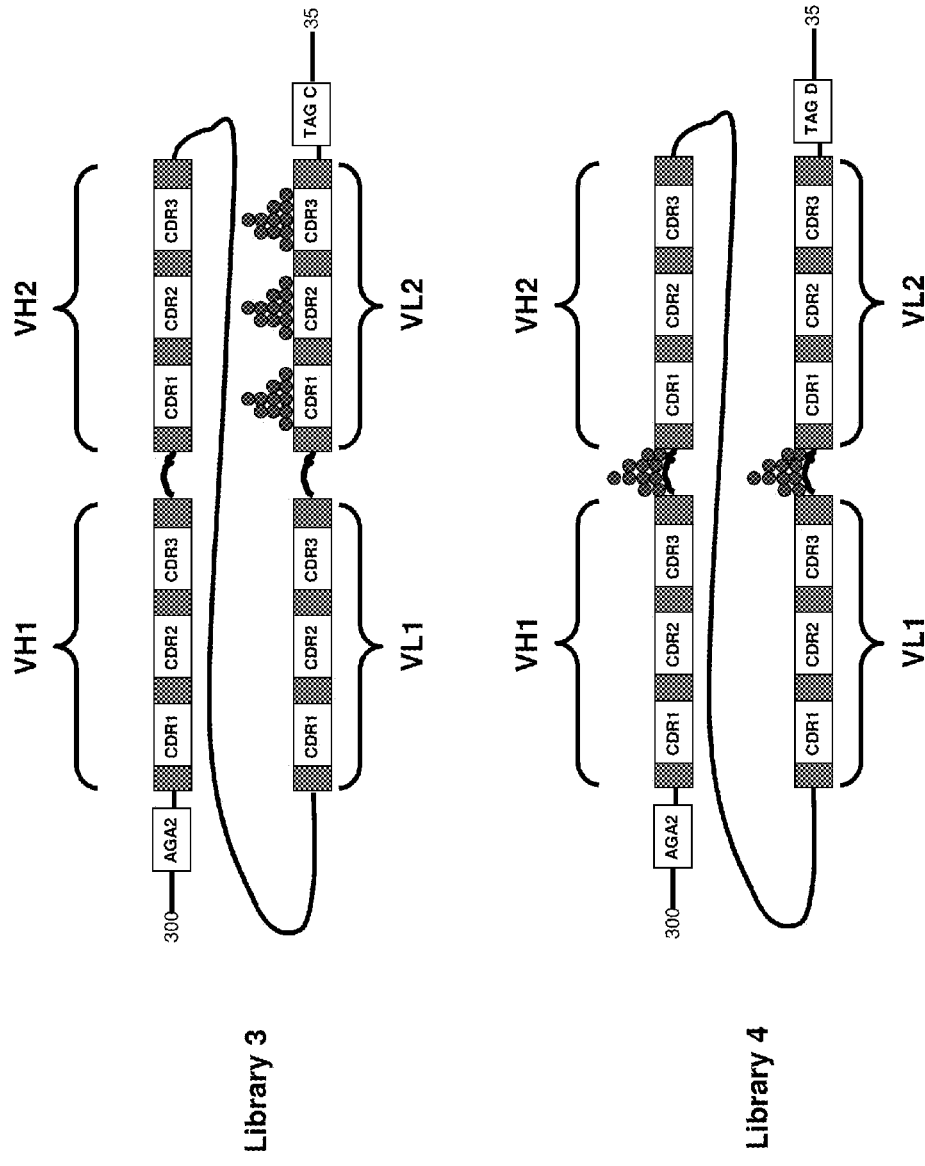
Figure 8:
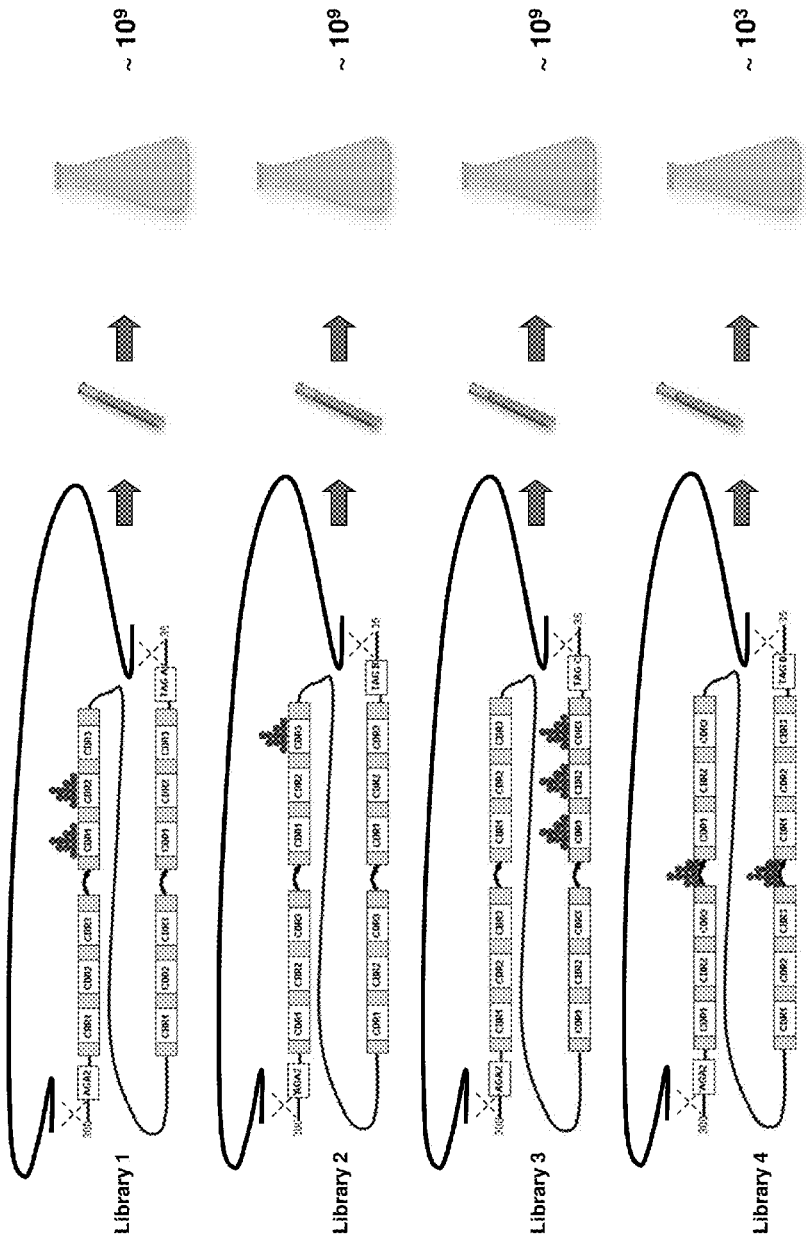
Figure 8:
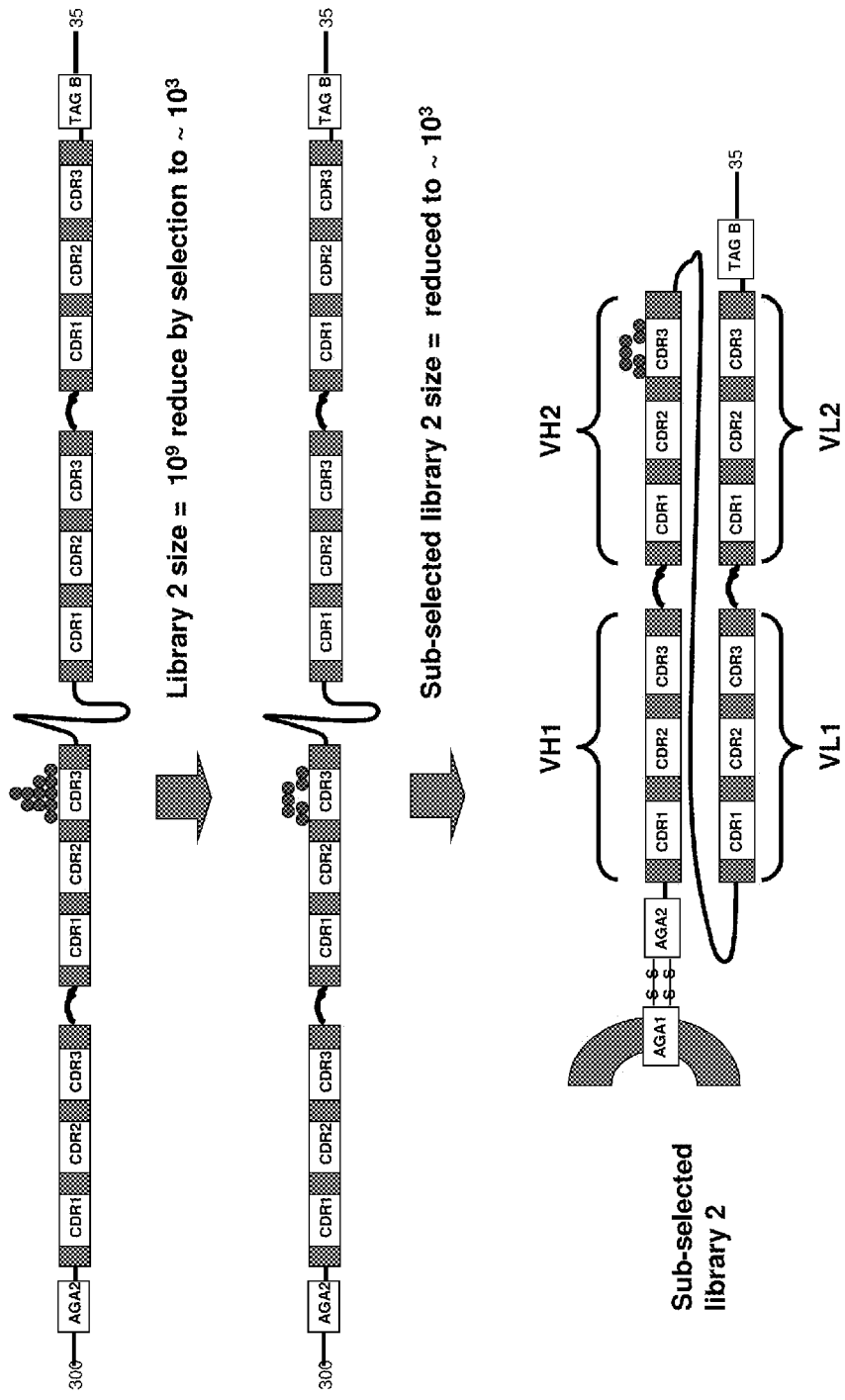
Figure 8:
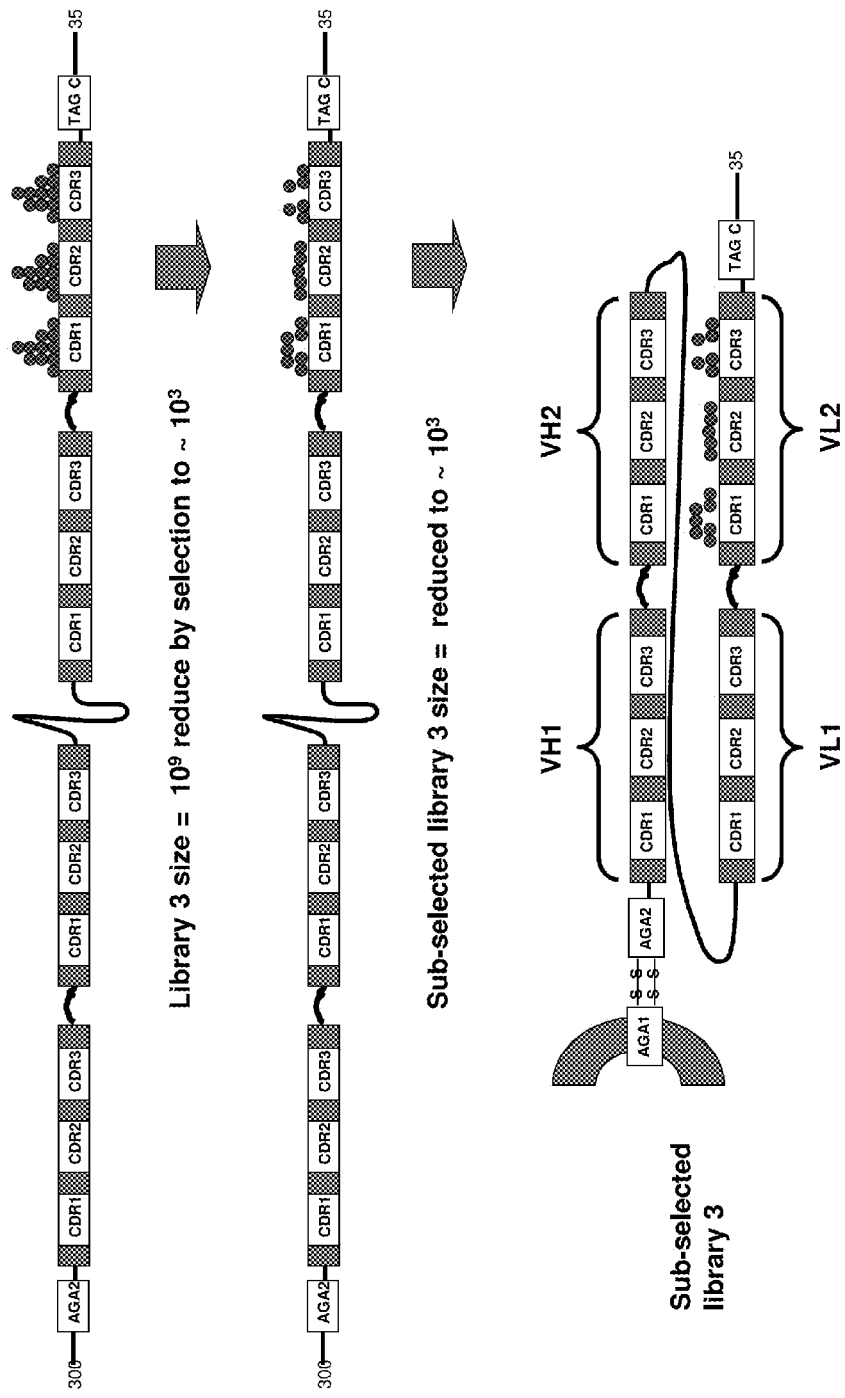
Figure 8:
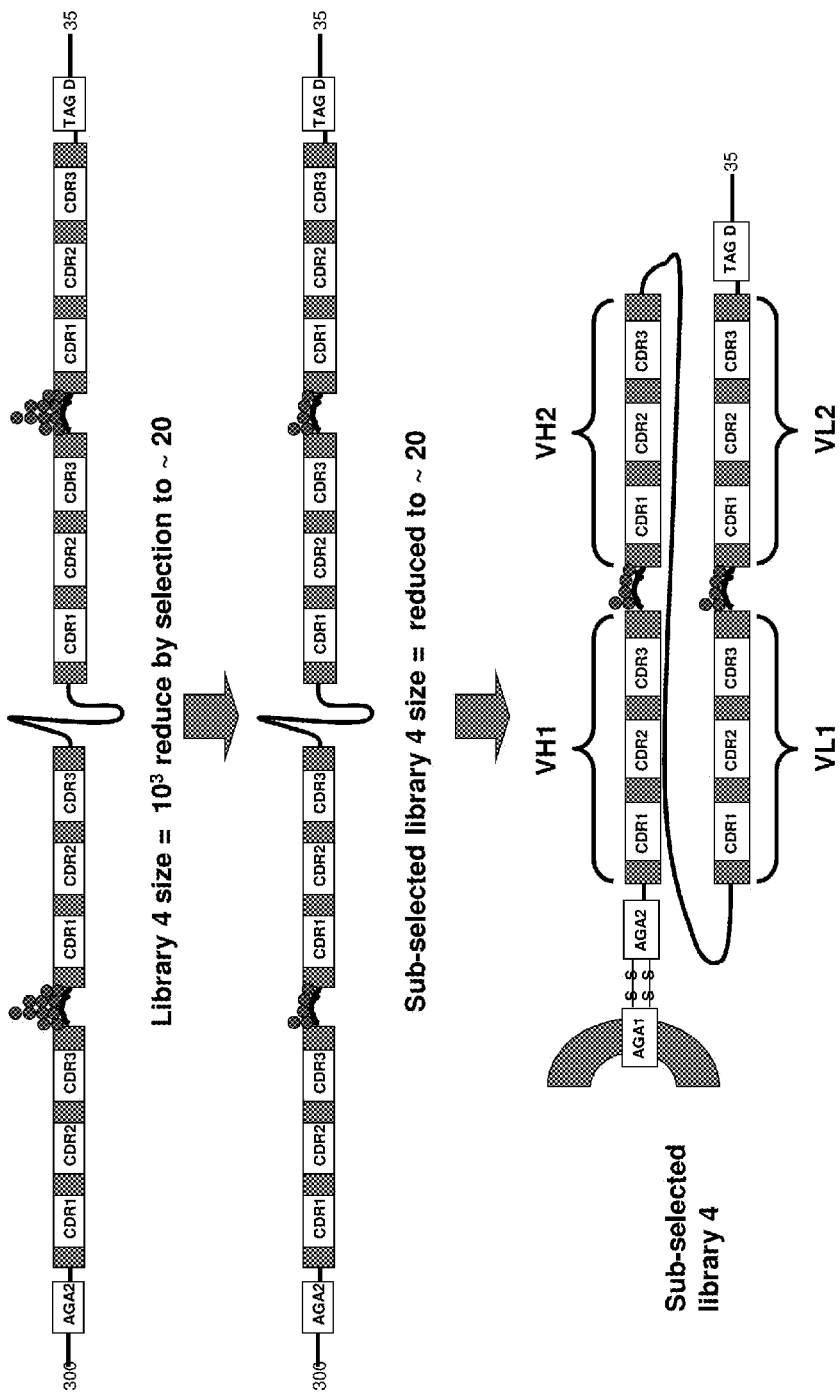
Figure 8:
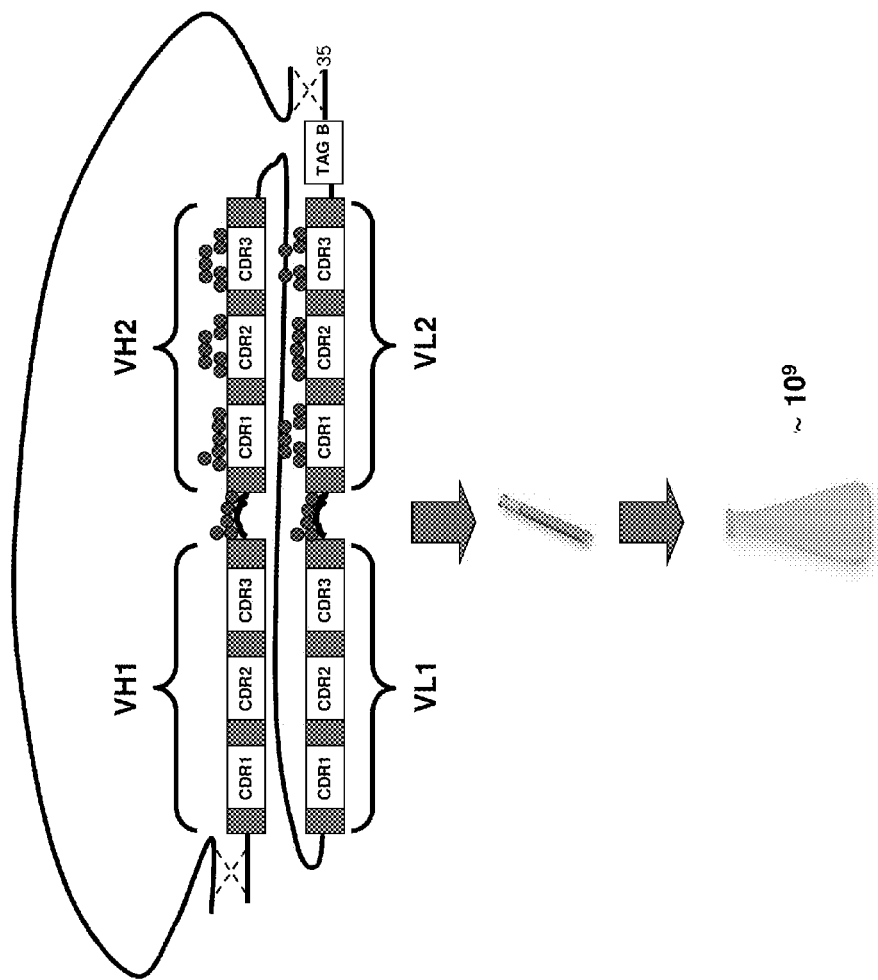
Figure 9:
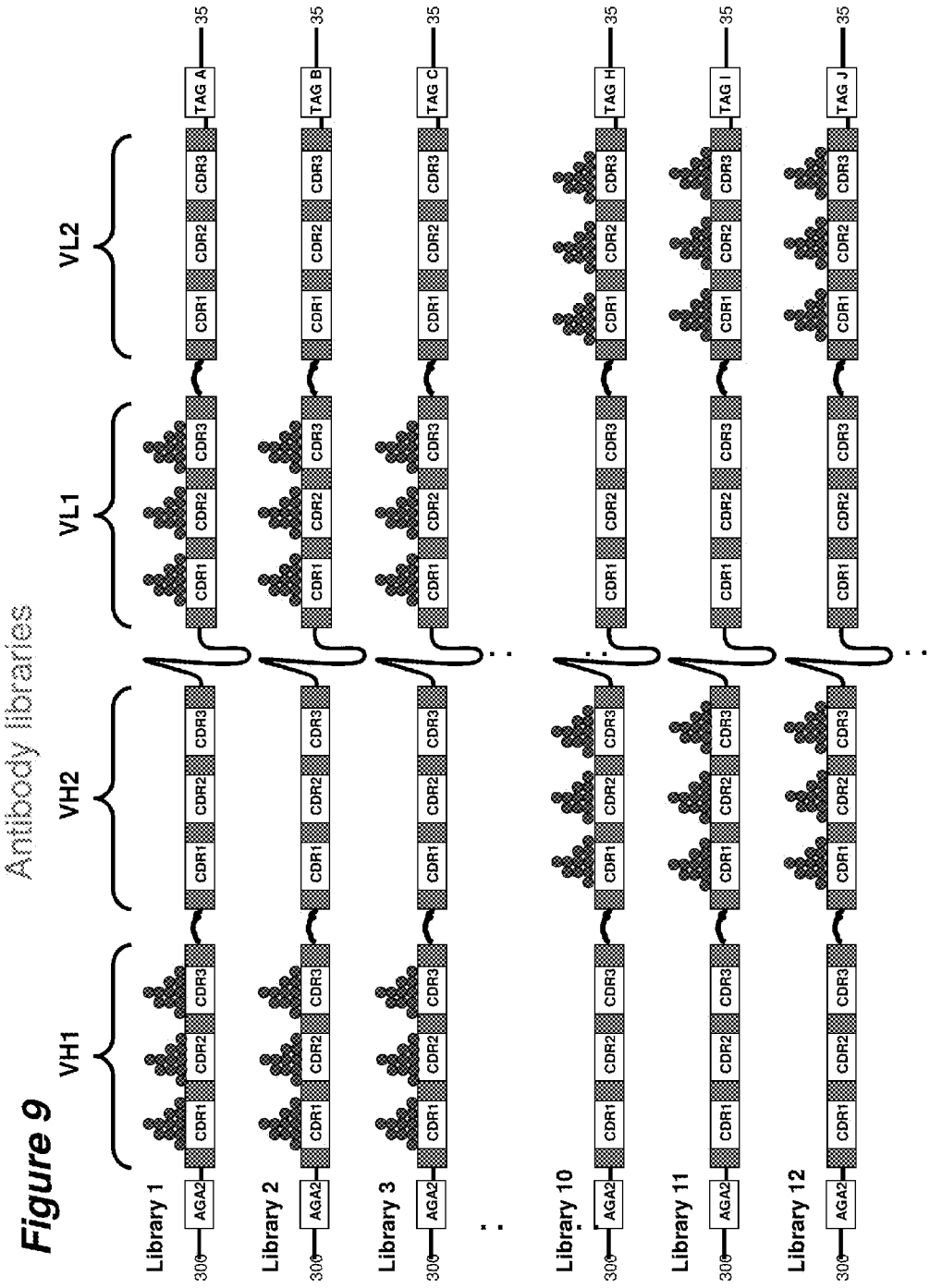
FIG. 9 is a schematic representation of exemplary scDVD libraries disclosed herein.

In one aspect, the disclosure provides libraries of single-chain multivalent binding proteins (e.g., scDVD molecules). Such libraries are particularly useful for selecting multivalent binding proteins with improved properties relative to a reference binding molecule (e.g., improved binding kinetics or thermostability). Exemplary libraries and methods are set forth in FIGS. 8 and 9.

In certain embodiments, the library of binding proteins comprises a polypeptide chain having the general formula VH1-(X1)n-VH2-X2-VL1-(X3)n-VL2, wherein VH1 is a first heavy chain variable domain, X1 is a linker with the proviso that it is not a constant domain, VH2 is a second heavy chain variable domain, X2 is a linker, VL1 is a first light chain variable domain, X3 is a linker with the proviso that it is not a constant domain, VL2 is a second light chain variable domain, and n is 0 or 1, wherein the VH1 and VL1, and the VH2 and VL2 respectively combine to form two functional antigen binding sites, and wherein the amino acid sequences of VH1, X1, VH2, X2, VL1, X3, and/or VL2 independently vary within the library. In one embodiment, the polypeptide chain is a scDVD.

In certain embodiments, the diverse library of binding proteins comprises a polypeptide chain having the general formula CH1-X0-VH1-(X1)n-VH2-X2-CL1-X4-VL1-(X3)n-VL2, wherein CH1 is a heavy chain constant domain, X0 is a linker with the proviso that it is not a constant domain, VH1 is a first antibody heavy chain variable domain, X1 is a linker with the proviso that it is not a constant domain, VH2 is a second antibody heavy chain variable domain, X2 is a linker, CL1 is a light chain constant domain, X4 is a linker with the proviso that it is not a constant domain, VL1 is a first antibody light chain variable domain, X3 is a linker with the proviso that it is not a constant domain, VL2 is a second antibody light chain variable domain, and n is 0 or 1, and wherein the VH1 and VL1, the VH2 and VL2 respectively combine to form two functional antigen binding sites, and wherein the amino acid sequences of VH1, X1, VH2, X2, VL1, X3, and/or VL2 independently vary within the library. Optionally, the CL1 domain can be a kappa (hcκ or cκ) or a lambda (hcλ or cλ) constant domain. In certain embodiments, CL1 is cκ. In one embodiment, the polypeptide chain is a scDVDFab.

In certain embodiments, X2 is a GS-rigid linker sequence. The GS rigid linker sequence can comprise an amino acid sequence selected from the group consisting of SEQ ID NOs:1-4.

In certain embodiments, the binding proteins further comprise a polypeptide chain having the general formula (VL1-(X1)n-VL2-X2-VH1-(X3)n-VH2, wherein VL1 is a first heavy chain variable domain, X1 is a linker with the proviso that it is not a constant domain, VL2 is a second heavy chain variable domain, X2 is a linker, VH1 is a first light chain variable domain, X3 is a linker with the proviso that it is not a constant domain, VH2 is a second light chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library. In one embodiment, the polypeptide chain is a scDVD.

In certain embodiments, the diverse library of binding proteins comprises a polypeptide chain having the general formula CL1-X0-VL1-(X1)n-VL2-X2-CH1-X4-VH1-(X3)n-VH2, wherein CL1 is a light chain constant domain, X0 is a linker with the proviso that it is not a constant domain, VL1 is a first antibody light chain variable domain, X1 is a linker with the proviso that it is not a constant domain, VL2 is a second antibody light chain variable domain, X2 is a linker, CH1 is a heavy chain constant domain, X4 is a linker with the proviso that it is not a constant domain, VH1 is a first antibody heavy chain variable domain, X3 is a linker with the proviso that it is not a constant domain, VH2 is a second antibody heavy chain variable domain, and n is 0 or 1, and wherein the VH1 and VL1, the VH2 and VL2 respectively combine to form two functional antigen binding site, and wherein the amino acid sequences of VH1, X1, VH2, X2, VL1, X3, and/or VL2 independently vary within the library. In certain embodiments, the CL1 light chain. Optionally, the CL1 domain can be a kappa (hcκ or cκ) or a lambda (hcλ or cλ) constant domain. In certain embodiments, CL1 is cκ. In one embodiment, the polypeptide chain is a scDVDFab.

In certain embodiments, X2 is a GS-rigid linker sequence. The GS rigid linker sequence can comprise an amino acid sequence selected from the group consisting of SEQ ID NOs:1-4.

Any region of the polypeptide chains can be varied independently in the libraries disclosed herein. In certain embodiments, the amino acid sequences of at least one CDR of VH1, VH2, VL1 or VL2 independently varies within the library. In one embodiment, the amino acid sequences of HCDR3 of VH1, VH2 independently vary within the library. In one embodiment, the amino acid sequences of HCDR1 and HCDR2 of VH1 or VH2 independently vary within the library. In one embodiment, the amino acid sequences of HCDR1, HCDR2 and HCDR3 of VH1 or VH2 independently vary within the library. In one embodiment, the amino acid sequences of HCDR3 of VL1 or VL2 independently vary within the library. In one embodiment, the amino acid sequences of HCDR1 and HCDR2 of VL1 or VL2 independently vary within the library. In one embodiment, the amino acid sequences of HCDR1, HCDR2 and HCDR3 of VL1 or VL2 independently vary within the library.

The linker regions X1, X2 and/or X3 can be also be varied independently in the libraries disclosed herein. Any length and sequence of linkers can be employed. Suitable amino acid sequences for use in linker X1, X2 and/or X3 are set forth in FIG. 2 herein. In other embodiments, X2 is selected from the amino acid sequences set forth in FIG. 11B. In specific embodiments, X2 is selected from the amino acid sequences set forth in FIG. 11B when the polypeptide chain includes CH and CL domain.

In certain embodiments, the libraries disclosed herein are used in cell surface display techniques (e.g., yeast display as described in Wittrup, et al. U.S. Pat. No. 6,699,658, incorporated herein by reference). Accordingly, in certain embodiments, each binding protein in the library further comprises a cell surface anchoring moiety linked to the N and/or C terminus. Any molecule that can display the binding proteins on the surface of a cell can be employed including, without limitation, cell surface protein and lipids. In certain embodiments, the anchoring moiety comprise the Aga2p polypeptide.

In certain embodiments, each binding protein in the library further comprises an epitope tag that that can be recognized by binding protein (e.g., an antibody). Suitable tags include without limitation, include His, HA, c-myc, Flag, HSV, S, AcV5, E2, E, and StrepII tags.

In certain embodiments, the library of binding proteins are employed to affinity mature a reference binding protein (e.g., scDVD or scDVDFab). Accordingly, in certain embodiments, the library of binding proteins share at least 70, 75, 80, 85, 90, 95, 96, 97, 98, or 99 amino acid sequence identity with a reference binding protein (e.g., scDVD or scDVDFab). In certain embodiments, the VH1 and VH2 of the reference binding protein specifically bind to different antigens.

In another aspect, the disclosure provides libraries of polynucleotides encoding the diverse library of binding proteins. The libraries can be produced by any art recognized means. In certain embodiments, the libraries are produced by combining portions of other libraries by overlap PCR In certain embodiments, libraries are produced by combining portions of other libraries by gap repair transformation in yeast cells. In certain embodiments, the nucleic acids encoding the binding proteins are operably linked to one or more expression control elements (e.g., promoters or enhancer elements).

In another aspect, the disclosure provides libraries of expression vectors comprising the diverse library of polynucleotides disclosed herein. Any vectors suitable of expressing the binding proteins can be employed.

In another aspect, the disclosure provides a library of transformed host cells, expressing the diverse library of binding proteins disclosed herein. In certain embodiments, the individual transformed cells in the library of transformed host cells express only one species from the diverse library binding proteins.

Any cells, prokaryotic or eukaryotic, are suitable for use as host cells. In certain embodiments, the host cells are yeast including, without limitation, *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula rubra, Schizosaccharomyces pombe* and *Yarrowia lipolytica*.

In certain embodiments, the expressed binding proteins are anchored on the surface of the host cell. Any means for anchoring can be employed. In certain embodiments, the binding proteins are anchored on the cell surface through Aga1p. This is usually achieved by the fusion of the Aga2p protein the N and/or C terminus of the binding protein.

IV. Single-chain Multivalent Binding Protein Screening Methods

In another aspect, the disclosure provides a method of selecting a binding protein (e.g., scDVD or scDVDFab) that specifically binds to a target antigen. The method generally comprises: a) providing a diverse library of transformed host cells expressing a diverse library of binding proteins disclosed herein; b) contacting the host cells with the target antigen; and c) selecting a host cell that bind to the target antigen, thereby identifying a binding protein that specifically binds to a target antigen.

In another aspect, the disclosure provides a method of selecting a binding protein that specifically binds to a first and a second target antigen simultaneously. The method generally comprises: a) providing a diverse library of transformed host cells expressing a diverse library of binding proteins disclosed herein; b) contacting the host cells with the first and second target antigen; and c) selecting a host cell that bind to the first and second target antigen, thereby identifying a binding protein that specifically binds to a first and a second target antigen simultaneously.

In certain embodiments of the foregoing methods, host cells that bind to the first and/or second antigen are selected by Magnetic Activated Cell Sorting using magnetically labeled antigen. In certain embodiments of the foregoing methods, host cells that bind to the first and/or second antigen are selected by Fluorescence Activated Cell Sorting using fluorescently labeled antigen.

Any host cells, prokaryotic or eukaryotic, are suitable for use in the foregoing methods. In certain embodiments, the host cells are yeast including, without limitation, *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula* rubra, *Schizosaccharomyces pombe* and *Yarrowia lipolytica*.

In certain embodiments, the expressed binding proteins are anchored on the surface of the host cell. Any means for anchoring can be employed. In certain embodiments, the binding proteins are anchored on the cell surface through Aga1p. This is usually achieved by the fusion of the Aga2p protein to one or more chain of the binding protein.

After selection of antigen-binding host cells, the polynucleotides encoding the binding proteins expressed by those cells can be isolated using any standard molecular biological means. These polynucleotides can be isolated and re-expressed in another cellular or acellular system as desired. Alternatively, these polynucleotides can be further modified and screened using the methods disclosed herein. In certain embodiments, the isolated polynucleotides are recombined with other polynucleotides (including libraries disclosed herein) to produce new, hybrid polynucleotides encoding novel binding proteins.

In certain embodiments, multiplex methods of screening libraries are employed. In such methods, each individual library is barcoded by one or more epitope tags that allows for differentiating one library or a subgroup or libraries from another library or a subgroup of libraries. Unique tag or tags are peptide sequences attached at the N-, C-, or both termini, or in the linker between VH and VL domains. The libraries are differentiated by binders (e.g., antibodies) to the epitope tags using flow cytometry or fluorescence activated cell sorting. The method of differentiation of libraries can be additive (a library having one or more tags distinct from the others) or subtractive (a library missing one ore more tags from the others). The libraries can be kept separately or combined (i.e. multiplexed) for analysis or cell sorting.

In the multiplex methods, the libraries are generally introduced to organisms that are amenable to magnetic and fluorescent activated cell sorting including, but not limited to, bacteria, yeast, and mammalian cells.

The libraries separated and distinguished by one or more tags can differ according to one or more of the following attributes: 1) antibody germline subgroups or sequences, light chain isotypes (kappa vs. lambda), or combinations thereof (e.g. specific VH/VL pairs); 2) natural or synthetic (or a combination thereof) antibody or TCR sequences; 3) cell type (B, T, plasma cells, etc); 4) tissues (peripheral blood, spleen, lymph node, bone marrow, tonsil, cord blood, etc); 5) species (human, mouse, rat, llama, rabbit, chicken, hamster, shark, etc); 6) protein scaffolds (antibodies, T cell receptors, etc); ormats (antibody and its fragments scFv, Fab, dAb, DVD-Ig, DVD-Fab, scDVD, scDVDFab, etc); 7) diversity and locations (framework vs. CDR diversity, HCDR3 size and diversity, HC vs. LC diversity, DVD-Ig linkers, domain orientation, etc; and/or 8) operation logistics (operators, lab locations, cell sorters, etc)

In certain embodiments, multiple diverse libraries are created, where each library contains clones that vary at a different discreet region of a reference binding protein. Each library is then screened separately for binding to the desired antigen(s) and the selected clones from each library are recombined to from a new library for screening. For example, to facilitate the affinity maturation of a reference binding protein, two distinct, diverse libraries can be created: a first diverse library in which only the HCDR1 and HCDR2 regions of a reference antibody are varied; and a second diverse library in which only the HCDR3 region of a reference antibody are varied. The first and the second library can be screened using the methods disclosed herein (e.g., using yeast display) to identify binding molecules with improved antigen binding characteristics. The polynucleotides encoding the selected binding proteins can then be recombined (e.g., by overlap PCR or yeast GAP repair) to form a third library comprising the HCDR1 and HCDR2 regions from the first library and the HCDR3 regions form second library. This third library can then be screened using the methods disclosed herein to identify binding proteins with further improved antigen binding characteristics. Exemplary libraries and methods are set forth in FIGS. 8 and 9.

Binding proteins selected using the methods disclosed herein can be isolated and re-expressed in another cellular or acellular system as desired.

V. Engineered Multivalent Binding Proteins

In certain preferred embodiments, the single-chain multivalent binding proteins produced using the methods and compositions disclosed herein exhibit improved properties (e.g., affinity or stability) with respect to a corresponding parental reference binding protein. For example, the engineered binding protein may dissociate from its target antigen with a $k_{off}$ rate constant of about $0.1s^{-1}$ or less, as determined by surface plasmon resonance, or inhibit the activity of the target antigen with an $IC_{50}$ of about $1\times10^{-6}M$ or less. Alternatively, the binding protein may dissociate from the target antigen with a $k_{off}$ rate constant of about $1\times10^{-2}s^{-1}$ or less, as determined by surface plasmon resonance, or may inhibit activity of the target antigen with an $IC_{50}$ of about $1\times10^{-7}M$ or less. Alternatively, the binding protein may dissociate from the target with a $k_{off}$ rate constant of about $1\times10^{-3}s^{-1}$ or less, as determined by surface plasmon resonance, or may inhibit the target with an $IC_{50}$ of about $1\times10^{-8}M$ or less. Alternatively, binding protein may dissociate from the target with a $k_{off}$ rate constant of about $1\times10^{-4}s^{-1}$ or less, as determined by surface plasmon resonance, or may inhibit its activity with an $IC_{50}$ of about $1\times10^{-9}M$ or less. Alternatively, binding protein may dissociate from the target with a $k_{off}$ rate constant of about $1\times10^{-5}s^{-1}$ or less, as determined by surface plasmon resonance, or inhibit its activity with an $IC_{50}$ of about $1\times10^{-10}M$ or less. Alternatively, binding protein may dissociate from the target with a $k_{off}$ rate constant of about $1\times10^{-5}s^{-1}$ or less, as determined by surface plasmon resonance, or may inhibit its activity with an $IC_{50}$ of about $1\times10^{-11}M$ or less.

In certain embodiments, the engineered binding protein comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the binding protein can comprise a light chain constant region, either a kappa light chain constant region or a lambda light chain constant region. The binding protein comprises a kappa light chain constant region. In certain embodiments, the scDVD is reformatted into a DVD-Ig or a DVD-Fab molecule (scDVDFab).

In certain embodiments, the engineered binding protein comprises an engineered effector function known in the art (see, e.g., Winter, et al. U.S. Pat. Nos. 5,648,260; 5,624,821). The Fc portion of a binding protein mediates several important effector functions e.g. cytokine induction, ADCC, phagocytosis, complement dependent cytotoxicity (CDC) and half-life/clearance rate of binding protein and antigen-binding protein complexes. In some cases these effector functions are desirable for therapeutic binding protein but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of binding proteins. In still another embodiment at least one amino acid residue is replaced in the constant region of the binding protein, for example the Fc region of the binding protein, such that effector functions of the binding protein are altered.

In certain embodiments, the engineered binding protein is derivatized or linked to another functional molecule (e.g., another peptide or protein). For example, a labeled binding protein disclosed herein can be derived by functionally linking a binding protein or binding protein portion disclosed herein (by chemical coupling, genetic fusion, non-covalent association or otherwise) to one or more other molecular entities, such as another binding protein (e.g., a bispecific binding protein or a diabody), a detectable agent, a cytotoxic agent, a pharmaceutical agent, and/or a protein or peptide that can mediate associate of the binding protein with another molecule (such as a streptavidin core region or a polyhistidine tag).

Useful detectable agents with which a binding protein or binding protein portion disclosed herein may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding protein may also be derivatized with detectable enzymes, such as alkaline phosphatase, horseradish peroxidase, glucose oxidase and the like. When a binding protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding protein may also be derivatized with biotin, and detected through indirect measurement of avidin or streptavidin binding.

In other embodiment, the engineered binding protein is further modified to generate glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the engineered binding protein or antigen-binding portion disclosed herein is modified. For example, an aglycoslated binding protein can be made (i.e., the binding protein lacks glycosylation). Glycosylation can be altered to, for example, increase the affinity of the binding protein for antigen. Such carbohydrate modifications can be accomplished by, for example, altering one or more sites of glycosylation within the binding protein sequence. For example, one or more amino acid substitutions can be made that result in elimination of one or more variable region glycosylation sites to thereby eliminate glycosylation at that site. Such aglycosylation may increase the affinity of the binding protein for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, an engineered binding protein disclosed herein can be further modified with an altered type of glycosylation, such as a hypofucosylated binding protein having reduced amounts of fucosyl residues or a binding protein having increased bisecting GlcNAc structures. Such altered glycosylation patterns have been demonstrated to increase the ADCC ability of binding proteins. Such carbohydrate modifications can be accomplished by, for example, expressing the binding protein in a host cell with altered glycosylation machinery. Cells with altered glycosylation machinery have been described in the art and can be used as host cells in which to express recombinant binding proteins disclosed herein to thereby produce a binding protein with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety. Using techniques known in the art a practitioner may generate binding proteins exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

VI. Production of Multivalent Binding Proteins

Engineered binding proteins of the present disclosure may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the binding proteins disclosed herein in either prokaryotic or eukaryotic host cells, expression of binding proteins in eukaryotic cells is preferable, and most preferable in mammalian host cells, because such eukaryotic cells (and in particular mammalian cells) are more likely than prokaryotic cells to assemble and secrete a properly folded and immunologically active binding protein.

Preferred mammalian host cells for expressing the recombinant binding proteins disclosed herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding binding protein genes are introduced into mammalian host cells, the binding proteins are produced by culturing the host cells for a period of time sufficient to allow for expression of the binding protein in the host cells or, more preferably, secretion of the binding protein into the culture medium in which the host cells are grown. Binding proteins can be recovered from the culture medium using standard protein purification methods.

Host cells can also be used to produce functional binding protein fragments, such as Fab fragments or scFv molecules. It will be understood that variations on the above procedure are within the scope of the present disclosure. For example, it may be desirable to transfect a host cell with DNA encoding functional fragments of either the light chain and/or the heavy chain of a binding protein of this disclosure. Recombinant DNA technology may also be used to remove some, or all, of the DNA encoding either or both of the light and heavy chains that is not necessary for binding to the antigens of interest. The molecules expressed from such truncated DNA molecules are also encompassed by the binding proteins disclosed herein. In addition, bifunctional binding proteins may be produced in which one heavy and one light chain are a binding protein disclosed herein and the other heavy and light chain are specific for an antigen other than the antigens of interest by crosslinking a binding protein disclosed herein to a second binding protein by standard chemical crosslinking methods.

In a preferred system for recombinant expression of a binding protein, or antigen-binding portion thereof, disclosed herein, a recombinant expression vector encoding both the binding protein heavy chain and the binding protein light chain is introduced into dhfr-CHO cells by calcium phosphate-mediated transfection. Within the recombinant expression vector, the binding protein heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the binding protein heavy and light chains and intact binding protein is recovered from the culture medium. Standard molecular biology techniques are used to prepare the recombinant expression vector, transfect the host cells, select for transformants, culture the host cells and recover the binding protein from the culture medium. Still further the disclosure provides a method of synthesizing a recombinant binding protein disclosed herein by culturing a host cell disclosed herein in a suitable culture medium until a recombinant binding protein disclosed herein is synthesized. The method can further comprise isolating the recombinant binding protein from the culture medium.

II. Exemplification

The present disclosure is further illustrated by the following examples which should not be construed as further limiting. The contents of Sequence Listing, figures and all references, patents and published patent applications cited throughout this application are expressly incorporated herein by reference.

EXAMPLE 1

Generation of Single Chain Dual Variable Domain Molecules

The design of a scDVD molecule derived from a DVD-Ig is shown schematically in FIG. 1. For comparison, the schematic diagrams of a DVD-Ig (FIG. 1B) and a scFv (FIG. 1C) have also been presented. The scDVD protein includes both the variable heavy and light chains of a DVD-Ig in their entirety with the carboxyl terminus of the VH domains tethered to the amino terminus of the VL domains through a Gly$_4$Ser peptide linker (SEQ ID NO:54) of 30, 35, 40 or 45 amino acids. VH1 and VH2 are paired connected with a specific linker sequence of 6 to 14 amino acids. VL1 and VL2 are paired connected with a specific linker sequence (SL) of 6 amino acids. Sequences encoding the variable regions were PCR amplified from DVD-Ig expression vectors. Primers were designed in such a way that amplified DNAs have the necessary overlap sequence to perform additional overlapping PCRs. The final fragment contains the VH domains, the long Gly$_4$Ser linker (SEQ ID NO:54), the VL domains and a peptide tag used to monitor expression of the scDVD on the surface of yeast. The construct is cloned by homologous recombination into a pYD yeast expression vector using DH5α chemically competent bacteria. Clones from the transformation were screened by bacteria colony PCR for the presence of the correct construct.

Figure 2:
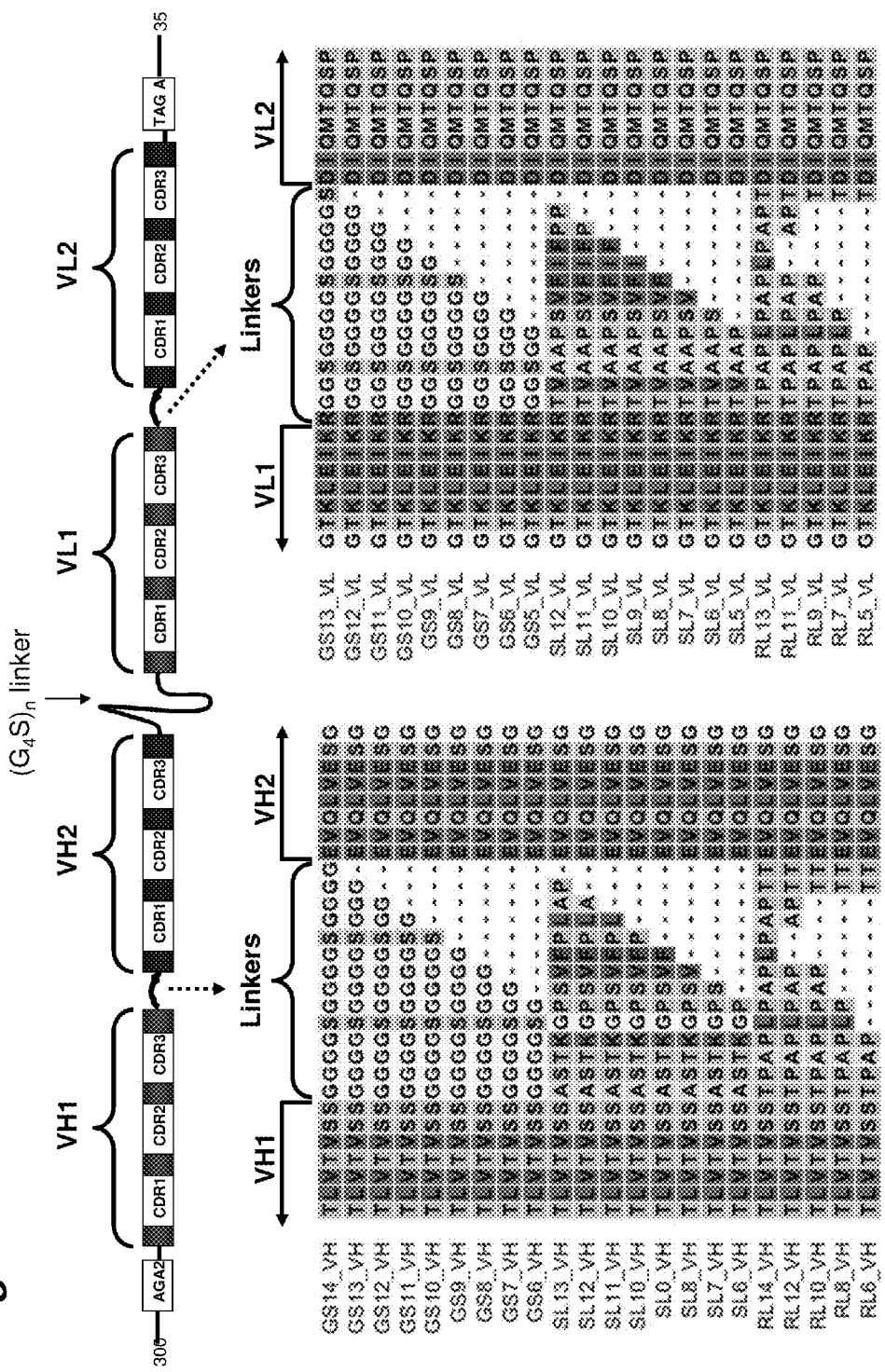
FIG. 2 is a schematic representation of an scDVD molecule and exemplary inter-variable domain linker amino acid sequences. The linkers between the VH1 and VH2 domains have amino acid sequences of SEQ ID NOs:9-30 listed from top to bottom. The linkers between the VL1 and VL2 domains have amino acid sequences of SEQ ID NOs:31-52 listed from top to bottom.

Several different linker sequences were evaluated for linking the VH domains or VL domains (see FIG. 2). The SL linkers correspond to the first 6 to 14 amino acids amino acids of the IgG1 constant region (ASTKGPSVFPLAPS (SEQ ID NO:55)), or corresponding to the first 6 to 14 amino acids of the IgK constant region (RTVAAPSVFIFPPS (SEQ ID NO:56)). The GS linkers correspond to 6 to 14 amino acids with repeats of Gly$_4$Ser (SEQ ID NO:54). The RL linkers correspond to sequences of 6 to 14 amino acids rich in Proline.

EXAMPLE 2 scDVD Expression on the Surface of Yeast

Figure 3:
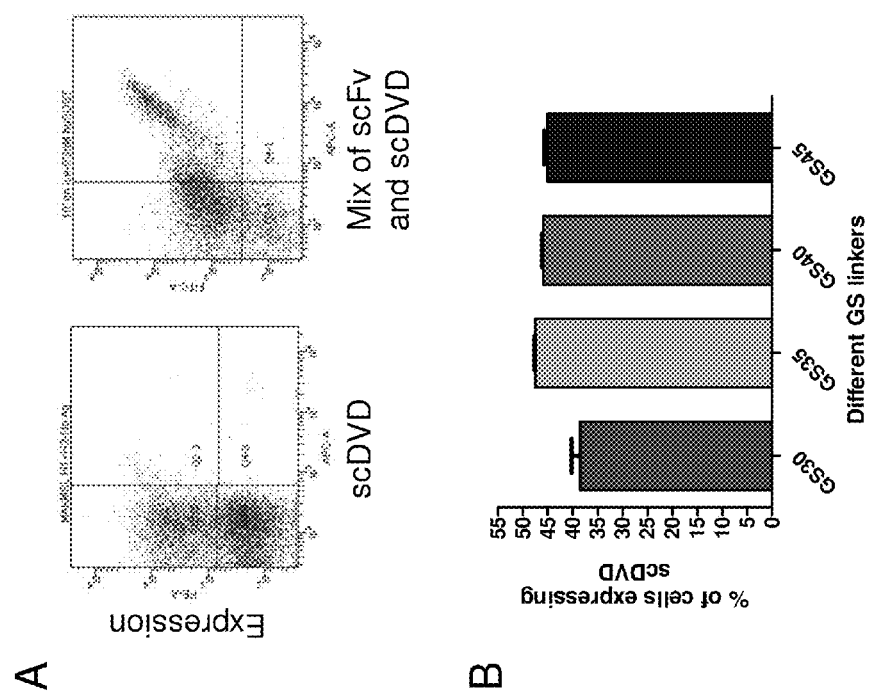
FIG. 3 depicts the results of flow cytometry assays measuring the cell surface expression of scDVD or scFv on yeast cells.

The expression of scDVD on the surface of yeast and the suitability of the selected epitope tags for monitoring expression were evaluated. scDVD expression on the surface of yeast was monitored by flow cytometry analysis using antibodies against scDVD epitope tags. The expression of scDVD on the surface of yeast was found to be comparable to that observed for scFv molecules, with about 50% of the yeast cells expressing the scDVD construct (FIG. 3A). However, scDVD expression shows a lower mean fluorescence intensity compared to scFv, suggesting a lower number of scDVD molecules were expressed by single cell. FIG. 3A (right dot-plot) shows this difference when two different yeast cultures (one expressing scDVD and another expressing scFv) are labeled together in the same tube. Both constructs are expressed in about 50% of the cells (data not shown) but scFv clones have a higher mean fluorescence.

The length of the long Gly$_4$Ser linker (SEQ ID NO:54) did not greatly impact the ability of the cells to express the scDVD. A Gly$_4$Ser linker (SEQ ID NO:54) of 30 amino acids seemed to have a negative impact on the expression while there was no difference in expression when using Gly$_4$Ser (SEQ ID NO:54) of 35, 40 or 45 amino acids (FIG. 3B).

EXAMPLE 3 scDVD Retains the Ability of DVD-Ig to Bind Both Targets

Figure 4A:
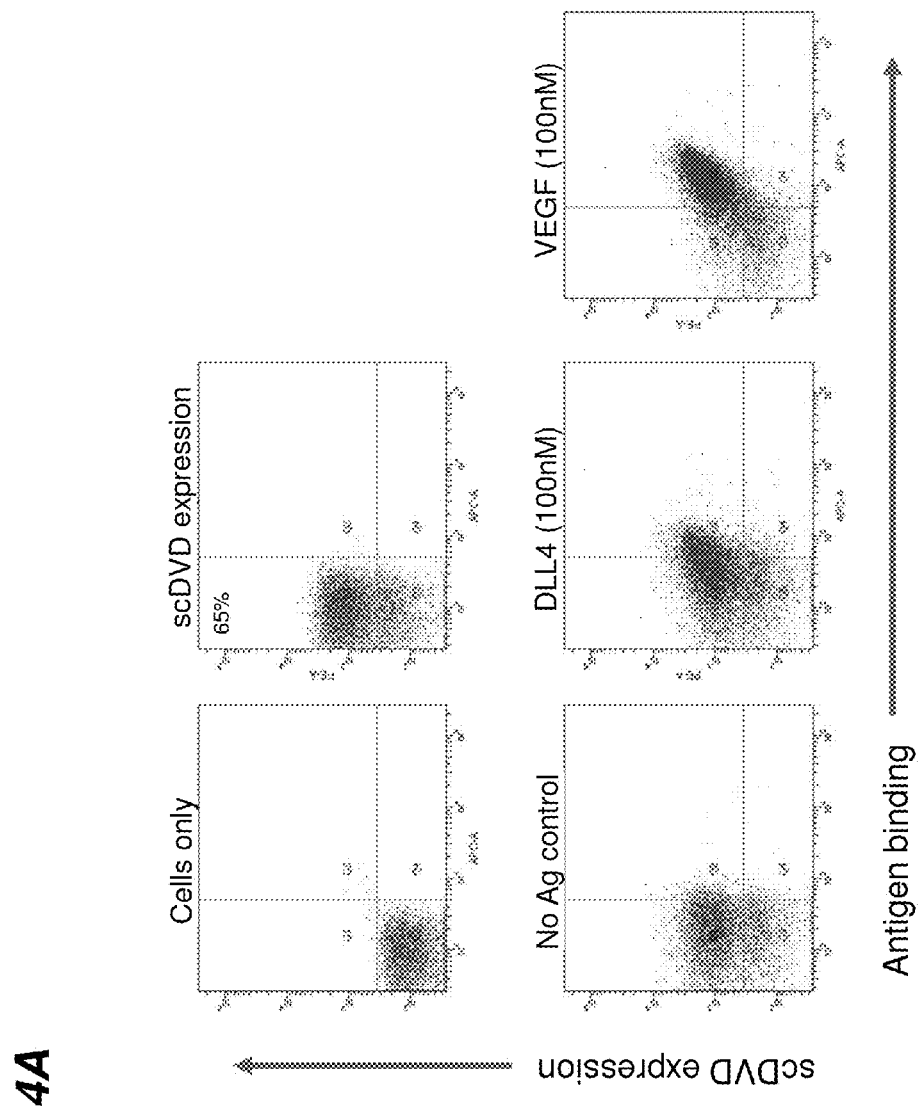
FIG. 4 depicts the results of flow cytometry assays measuring the binding of (A) DLL4 and/or VEGF to yeast cells expressing cell surface DLL4/VEGF-binding scDVD, and (B) SOST and/or TNFa to yeast cells expressing cell surface SOST/TNFa-binding scDVD.
Figure 4B:
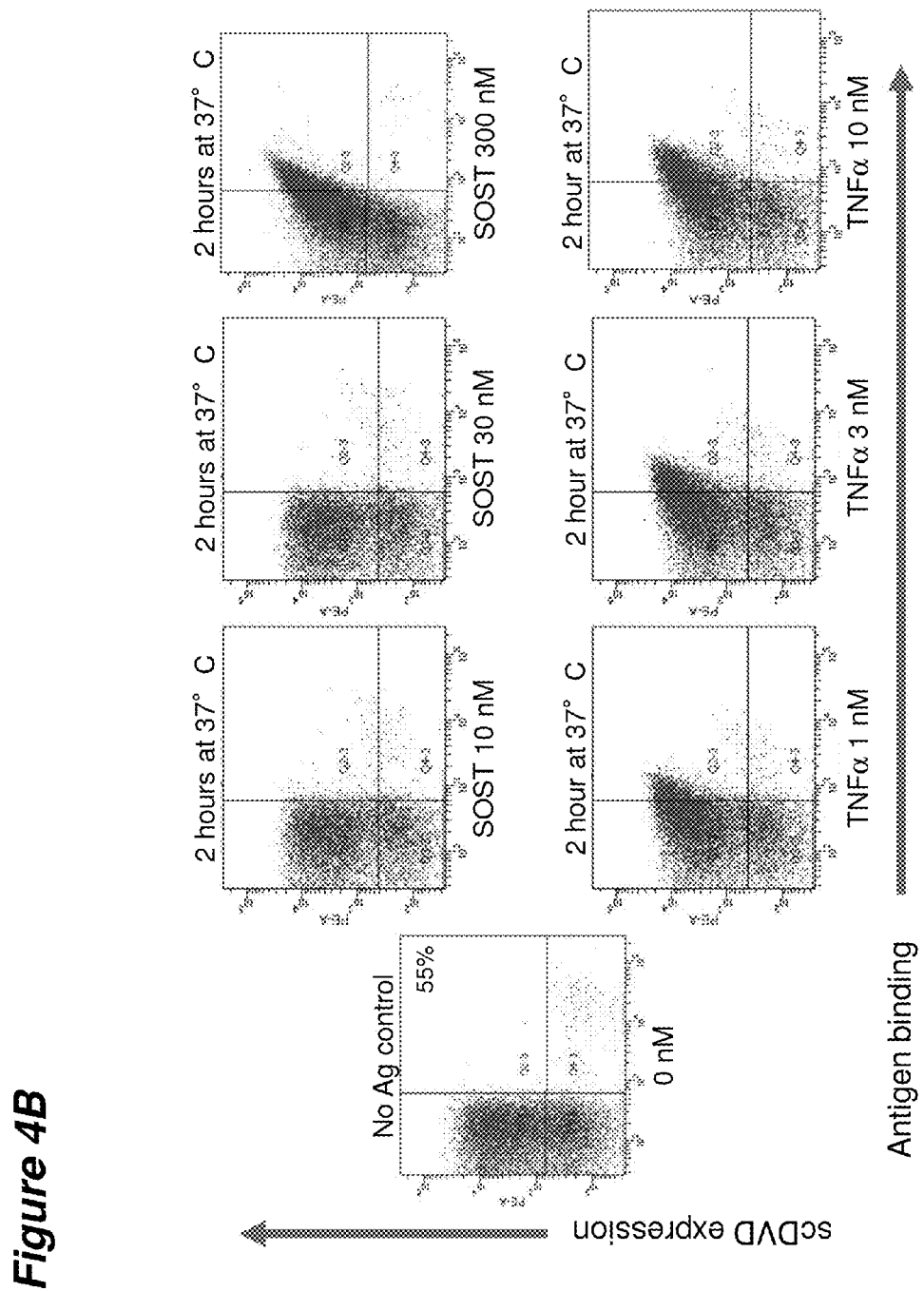

Two different DVD-Igs were expressed as scDVD on the surface of yeast using pYD vectors with three different tags (AcVS, E or StrepII peptide tags). Each construct was incubated with biotinylated antigens under the same conditions and concentrations. scDVD expression was monitored using epitope tags specific antibodies made in mouse, goat and rabbit, respectively. Fluorochrome labeled donkey anti-mouse, goat or rabbit antibodies were used as detection reagents. Mean fluorescence is shown in each individual dot-plot. DLL4/VEGF scDVD retains its ability to bind both DLL4 and/or VEGF (FIG. 4A). There is no difference in binding (mean fluorescence intensity) when the scDVD is incubated with DLL4, VEGF, or a mixture of the two antigens. The same findings were observed for TNF/SOST scDVD. This scDVD retains its ability to bind both TNF and/or Sclerostin (FIG. 4B). There is no difference in binding (mean fluorescence intensity) when the scDVD is incubated with TNF, SOST, or a mixture of the two antigens. Yeast cells express many copies of scDVD on the cell surface, accordingly, the simultaneous binding to both antigens could theoretically be due to some scDVD molecules on a cell binding to one antigen and other scDVD molecules on the same cell binding independently to the second antigen. However, the mean fluorescence do not change when the scDVD is incubated with one antigen, the other antigen or a mix of both antigens, suggesting that the scDVD molecules are binding both antigens simultaneously.

Figure 5:
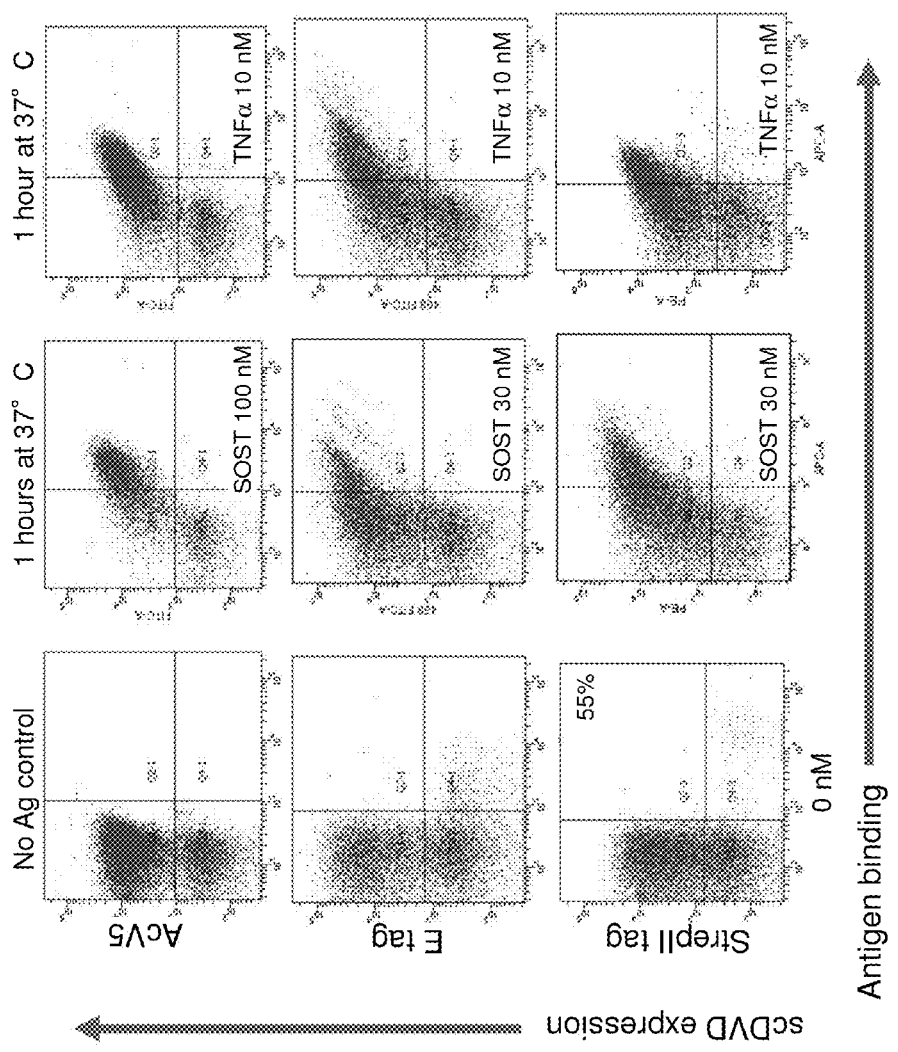
FIG. 5 depicts the results of flow cytometry assays measuring the binding of SOST and/or TNFa to yeast cells expressing cell surface SOST/TNFa-binding scDVD tagged with various epitope tags.

EXAMPLE 4 scDVD Binds Both Antigens Regardless the Tag Used to Monitor its Expression on the Surface of Yeast In yeast display, expression tags are used to monitor the antibody expression and to normalize the antigen-binding signal for expression, thus eliminating artifacts due to host expression bias. This allows for fine discrimination between mutants with different affinities towards their target. Experiments were performed to determine if any given functional DVD-Ig, when expressed as a scDVD, maintains its binding capabilities towards its two cognate targets regardless of the tag used to monitor its expression on the surface of yeast. Specifically, TNF/SOST DVD-Ig was expressed as scDVD on the surface of yeast using three different tags (AcV5, E or StrepII peptide tags). The three constructs were exposed to the same biotinylated antigens (TNF and Sclerostin) under the same conditions and concentrations. scDVD expression was monitored using tag-specific antibodies made in mouse (anti-AcV5; Abcam), goat (anti-E; Abcam) and rabbit (anti-StrepII; GeneScript). Fluorochrome labeled donkey anti-mouse (PerCP), goat (PE) or rabbit (DyLight488) antibodies were used as detection reagents (see Tables 1-3 herein). Antigen binding was monitored by APC conjugated streptavidin or Dylight633 conjugated neutravidin. All samples were analyzed by flow cytometry. FIG. 5 shows that it is feasible to use different peptide tags to monitor scDVD expression and binding on the surface of yeast.

EXAMPLE 5

Figure 6A:
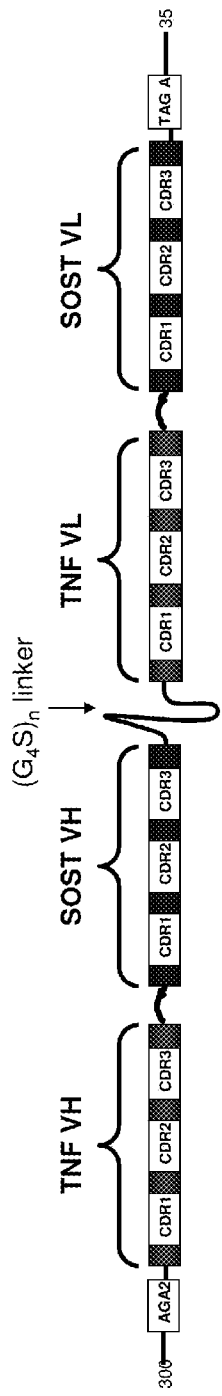
FIG. 6 depicts (A) the amino acid sequence of an exemplary SOST/TNFa-binding scDVD molecule (SEQ ID NO:57)(FIG. 6A discloses "(G₄S)ₙ," as SEQ ID NO:54), (B) an exemplary SOST/TNFa-binding scDVD library design, with the VH3-9, SOST VH, V1-16 and MSL10VL sequences represented by SEQ ID NOs:58-61, respectively.
(FIG. 6B discloses "(G₄S)ₙ," as SEQ ID NO:54) (C) the results of flow cytometry assays measuring the binding of SOST to yeast cells expressing parental or affinity matured cell surface SOST/TNFa-binding scDVD, and (D) the results of flow cytometry assays measuring the binding of SOST to yeast cells expressing parental or affinity matured cell surface SOST/TNFa-binding scDVD.
Figure 6B:
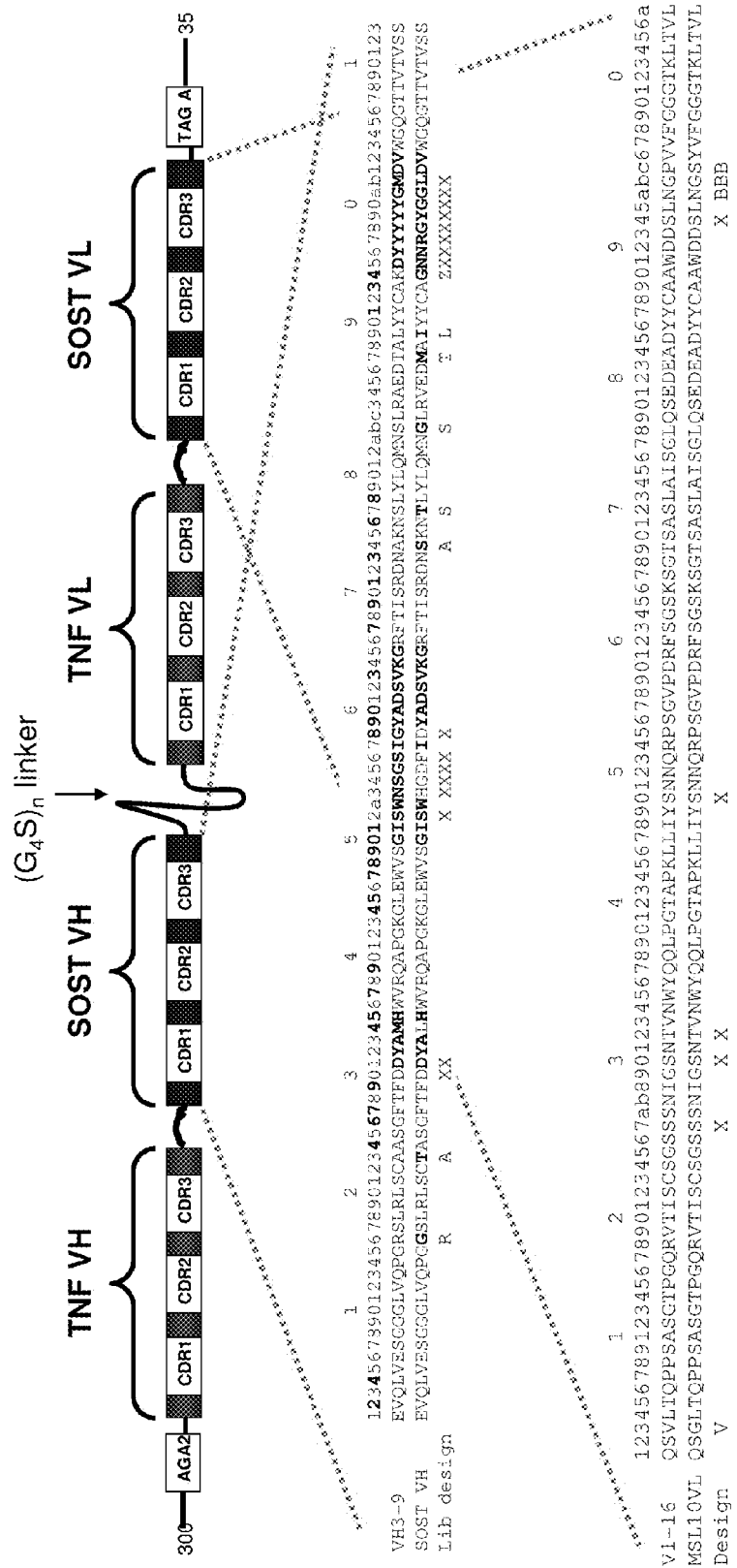

Binding Selection of a TNF/SOST scDVD Derived Library Demonstrate Expression and Binding Improvement Compare with the Parental scDVD In order to test the ability of scDVD format expressed on the surface of yeast to enhance and affinity mature DVD-Ig, an affinity maturation of a TNF/SOST DVD-Ig was performed using different libraries. These libraries were constructed to contain limited mutations in different CDRs of SOST variable domains. The TNF/SOST scDVD protein sequence is set forth in FIG. 6A. To design these libraries hypermutated CDR residues were identified from other human antibody sequences. The corresponding SOST CDR residues were then subjected to limited mutagenesis by PCR with primers having low degeneracy (79% parental nucleotide and 21% all other three nucleotides) at these positions to create three antibody libraries in the scDVD format suitable for yeast surface display. The first library (H1+H2) contained mutations in HCDR1 and HCDR2 of SOST VH domain. The second library (H3) contained mutations in HCDR3 of SOST VH domain and the third library (LC) contained mutations in all CDRs of SOST VL domain. To further increase the identity of SOST variable domains to the human germline framework sequence, a binary degeneracy (50% parental 50% germline) at certain positions were introduced into the libraries and certain residues were germline (see FIG. 6B). The introduced changes were as follows:

H1+H2 Library:
  Limited mutagenesis of residues: D30, D31, S52, H53, G54, D55, F56 and D58
  Germlining 7 residues: G16R, T23A, S74A, T77S, G82bS, M87T, I89L H3 Library:
  Limited mutagenesis of residues: N95, N96, R97, G98, Y99, G100, G100a, L100b
  Germlining 7 residues: G16R, T23A, S74A, T77S, G82bS, M87T, I89L
  Binary degeneracy between SOST VH and germline at G94K LC Library:
  Limited mutagenesis of residues: S27, S30, T32, S40, S94
  NNK randomization at residues N95a, G95b and S95c
  Binary degeneracy between SOST VL and germline at G3V These libraries (see FIG. 6B) were separately transformed and displayed on yeast cells and selected against low concentration of biotinylated Sclerostin and TNF by magnetic then fluorescence activated cell sorting. Each library was differently tagged by one of StrepII, FLAG or E peptide tags. scDVD expression and antigen binding were monitored by flow cytometry as described above using the antibodies described on Tables 2 and 3 herein.

Figure 6C:
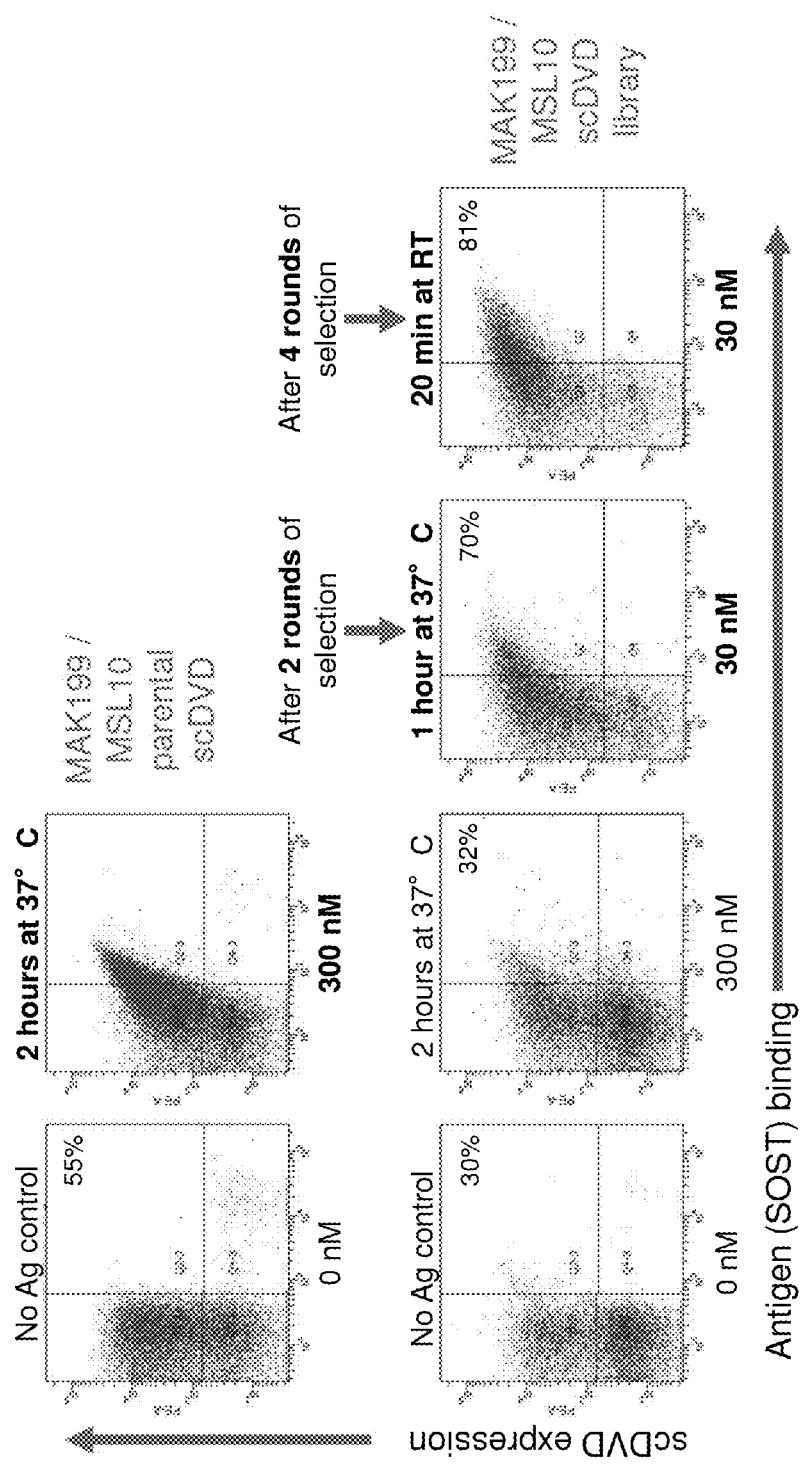

After 2 and 4 rounds of selection, the binding towards Sclerostin was notably improved compared to the binding of the parental molecule. Parental TNF/SOST scDVD binds to 300 nM of Sclerostin after an incubation for 1 hour at 37° C. No binding was observed when the parental molecule was incubated with 30 nM of Sclerostin. In contrast, after 2 rounds of selection the H3 library shows binding to 30 nM of Sclerostin, and after 4 round of selection the binding to 30 nM of Sclerostin is observed when the library output was incubated only for 20 minutes at room temperature (see FIG. 6C). Similar improvements were observed for the H1+H2 and LC libraries.

Figure 6D:
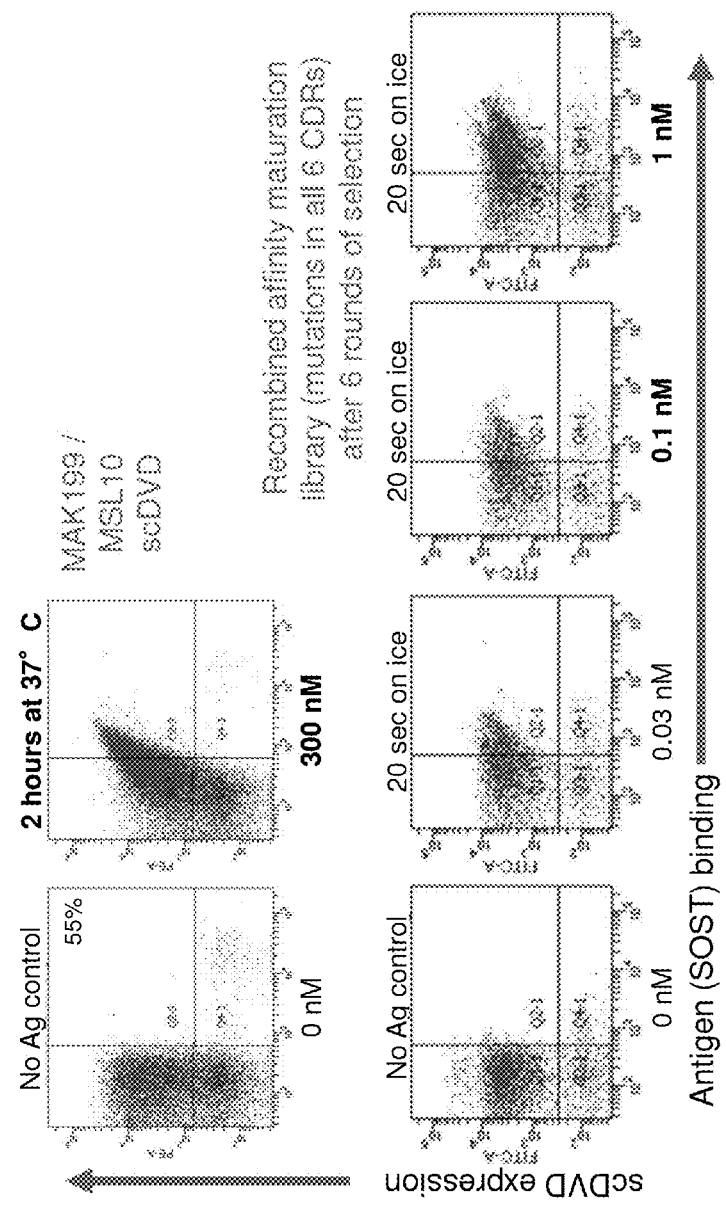

Once the diversity of each library is reduced to about $10^3$ the plasmid DNA from each output was isolated and the libraries are recombined by PCR into a new library (rHC+LC). This library was transformed into yeast cells and displayed on cell surfaces to be selected against biotinylated Sclerostin. After selection the improvement in affinity is very notorious. As pointed out the parental construct is able to bind Sclerostin at 300 nM when incubated for 1 hour at 37° C. rHC+LC library output after 6 round of selection is able to bind 0.1 nM of Sclerostin when incubated only for 20 seconds at 4° C. (FIG. 6D). Although, no formal quantification of the affinity is done, an improvement of more than 100 folds is expected based on this results. It is clear that scDVD based libraries could be selected and enriched for better binders.

EXAMPLE 6

Figure 7A:
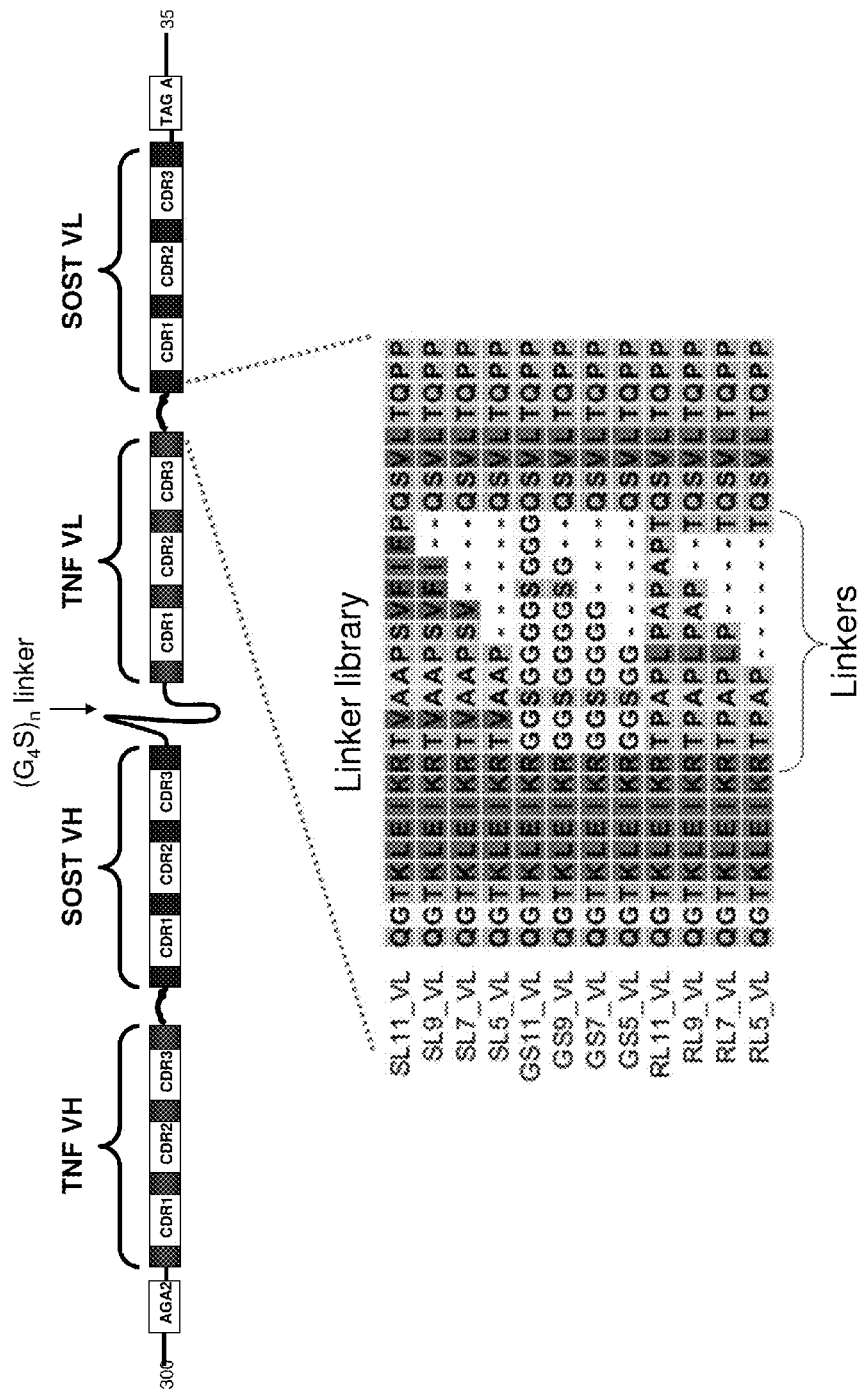
FIG. 7 depicts (A) a schematic representation of an scDVD molecule and exemplary inter-VL domain linker amino acid sequences of SEQ ID NOs:62-73 listed from top to bottom (FIG. 7A discloses "(G₄S)ₙ," as SEQ ID NO:54), and (B) and results (as fold enrichment) of yeast display screens of SOST/TNFa-binding scDVD library comprising various inter-VL domain linker amino acid sequences.

Binding Selection of TNF/SOST scDVD Libraries Shows Enrichment of SL Linkers Between VL Domains As discussed above, there is a clear need for linker engineering during the construction and optimization of DVD-Ig antibodies. Steric hindrance due to the proximity of the outer variable domain to the ligand binding site of the inner VD could, at least partially, be responsible for a reduced affinity of a domain when engineered as the inner variable domain. Accordingly, experiments were performed to determine if the scDVD approach could be used to engineer linkers to pair VHs or VLs in a DVD-Ig. To this end, a TNF/SOST scDVD library was made by introducing 12 different linkers: four SL linkers corresponding to the first 6, 8, 10 and 12 amino acids amino acids of the IgK constant region; four GS linkers with repeats of Gly$_4$Ser (SEQ ID NO:54) of 6, 8, 10 and 12 amino acids; and four proline-rich RL linkers corresponding to 6, 8, 10 and 12 amino acids (see FIG. 7A). Additionally, residues S94, N95a, G95b and S95c of the LCDR3 of SOST VL were mutated by NNK randomization. After four rounds of selection using different concentrations of Sclerostin under different conditions, the library output showed enrichment in RL linkers especially of the longest size (12 and 10 amino acids; between 3 to 7 folds). Also, the GS linkers were significantly reduced (between 6 to 8 fold) (see FIG. 7B). This data clearly demonstrates that scDVD-based yeast surface display allows for the optimization and engineering of linkers to pair VHs or VLs.

TABLE 1

Peptide tags used on a panel of yeast expression vectors

| Peptide Tag | DNA sequence | Protein sequence | pYDsTEV vectors |
|---|---|---|---|
| HIS* | CATCATCACCATCACCAT | HHHHHH | |
| V5 | GGTAAGCCTATCCCTAACCCTCTCCTCGGTCTCGATTCTACG | GKPIPNPLLGLDST | 13767_pYDs_TEV_total |
| c-MYC | GAACAAAAACTTATTTCTGAAGAAGATCTG | EQKLISEEDL | pYDsTEV_c-MYC |
| HA | TACCCATACGATGTTCCGGATTACGCT | YPYDVPDYA | pYDsTEV_HA |
| HSV | AGCCAGCCAGAACTCGCTCCTGAAGACCCAGAGGAC | SQPELAPEDPED | pYDsTEV_HSV |
| FLAG | GACTACAAGGACGACGACGACAAG | DYKDDDDK | pYDsTEV_FLAG |
| Strep II | TGGAGCCATCCGCAGTTTGAGAAG | WSHPQFEK | pYDsTEV_StrepII |
| E2 | TCCAGCACCTCGAGTGATTTTCGAGATCGC | SSTSSDFRDR | pYDsTEV_E2 |
| S | AAGGAAACCGCGGCTGCCAAGTTTGAACGCCAGCATATGGATAGC | KETAAAKFERQHMDS | pYDsTEV_S |
| E | GGAGCGCCTGTACCATATCCGGATCCGCTGGAACCGCGC | GAPVPYPDPLEPR | pYDsTEV_E |
| AcV5 | AGCTGGAAGGATGCGAGCGGCTGGAGC | SWKDASGWS | pYDsTEV_AcV5 |

*HIS tag is present in all pYDsTEV vectors downstream of all others tags.

TABLE 2

Commercially available anti-peptide tags antibodies used to monitor ScDVD antibody expression on yeast.

| Tag | Ab Source | Clone | Source | Catalog # |
|---|---|---|---|---|
| S | Mouse | SBSTAGa | Abcam | ab24838 |
| S | Rabbit | Polyclonal | | ab18588 |
| AcV5 | Mouse | AcV5 | Abcam. Rabbit S tag antibody | ab49581 |
| E2 | Mouse | 5E11 | Abcam. AcV5 tag antibody | ab977 |
| E | Rabbit | Polyclonal | Abcam T7 tag ® | ab3397 |
| E | Goat | Polyclonal | Abcam | ab95868 |
| E | Chicken | Polyclonal | | ab18695 |
| StrepII | Mouse | Strep-tag | Abcam. E tag antibody | MCA2489 |
| StrepII | Rabbit | Polyclonal | Abcam. E tag antibody | A00626 |
| HA | Mouse | HA-7 | Sigma | H9658 |
| HA | Goat | Polyclonal | Abcam | ab9134 |
| HA | Rat (IgG1) | 3F10 | Roche | 11-867-423 |
| c-myc | Mouse | 9E10 | Sigma | M4439 |
| c-myc | Rabbit | Polyclonal | Sigma | C3956 |
| Flag | Mouse | M2 | Sigma | F3165 |
| Flag | Rabbit | Polyclonal | Sigma | F7425 |
| HSV | Rabbit | Polyclonal | Sigma | H6030 |

TABLE 3

Commercially available secondary reagents used to monitor scFv antibody expression and binding on the surface of yeast

| Secondary reagent | Fluorocrome | Source | Catalog # |
|---|---|---|---|
| F(ab')2 Frag. Donkey Anti-Rat IgG | PerCp | Jackson ImmunoResearch | 712-126-150 |
| F(ab')2 Frag. Donkey Anti-Goat IgG | R-PE | Jackson ImmunoResearch | |
| F(ab')2 Frag. Donkey Anti-Rabbit IgG | DyLight-488 | Jackson ImmunoResearch | 705-116-147 |
| F(ab')2 Frag. Goat Anti-Rabbit IgG | R-PE | Jackson ImmunoResearch | |
| F(ab')2 Frag. Goat Anti-Rabbit IgG | Alexafluor 488 | Invitrogen | 711-486-152 |
| Chicken anti mouse IgG (H + L) | PerCP | Jackson ImmunoResearch | 111-116-144 |
| F(ab')2 Frag Donkey Anti-Mouse IgG | Alexafluor 633 | ThermoScientific | 715-126-151 |

EXAMPLE 7

Figure 10:
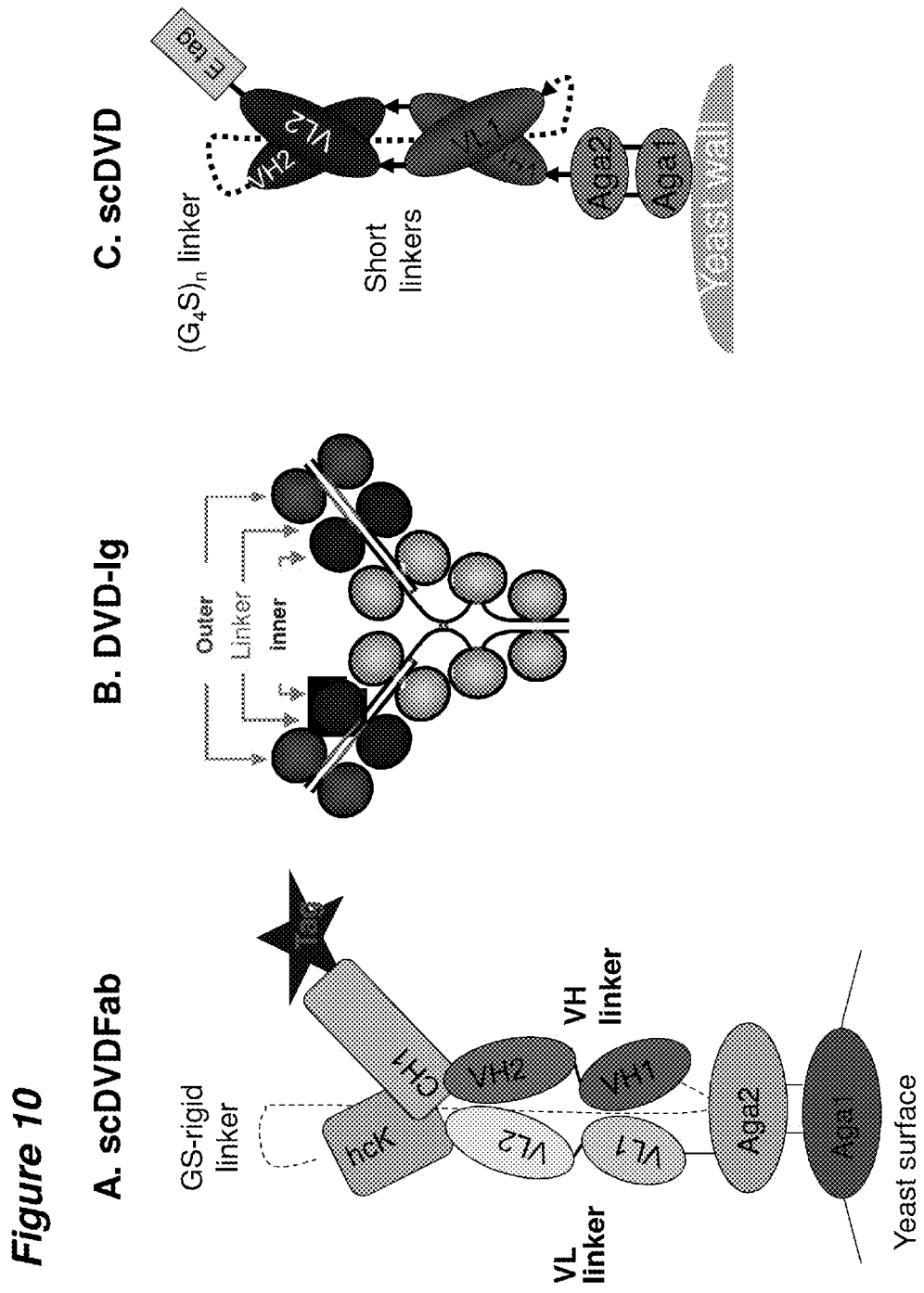
FIG. 10 depicts (A) an exemplary single chain dual variable domain Fab (scDVDFab) molecules, (B) an exemplary full-length DVD-Ig molecule, and (C) an exemplary a single chain DVD molecule (FIG. 10C discloses "(G₄S)₄" as SEQ ID:54.

Generation of a Single Chain Dual Variable Domain Fab (scDVDFab) Including Constant Regions Another design of a scDVDFab antibody derived from a DVD-Ig is shown schematically in FIG. 10. For comparison, the schematic diagrams of a DVD-Ig (FIG. 10B) and a scDVD (FIG. 10C) have also been presented. In this example, the scDVDFab protein includes the variable heavy (VH) and light (VL) chains of a DVD-Ig in their entirety with the CH1 region of the heavy chain and the kappa constant region (Cκ) of the light chain. As shown in FIG. 10A, The VL domains fused to the Cκ are tethered to the VH domains fused to the CH1 through a GS-rigid peptide linker of 41, 49, 57 or 65 amino acids from the carboxyl terminus of the Ck region to the amino terminus of the VH domains. These linkers are shown in greater detail below. VL1 and VL2 are paired connected with specific linkers already described and used in DVD-Igs and scDVD. The same is for VH1 and VH2 pair. FIG. 11A contains a schematic representation of a scDVDFab linear sequence.

Sequences encoding the variable regions were PCR amplified from the DVD-Ig expression vectors. Primers were designed in such a way that amplified DNAs had the necessary overlap sequence to perform additional overlapping PCRs. The final fragment contained the linear sequence represented in FIG. 11A plus a peptide tag used to monitor expression of the scDVDFab on the surface of yeast. The construct was cloned by homologous recombination into a pYD yeast expression vector using DH5a chemically competent bacteria. Clones from the transformation were screened by bacteria colony PCR for the presence of the right construct.

GS-rigid Linkers

The GS-rigid linkers were made by combinations of different Gly/Ser segments and proline rich rigid segments. The sequences of the linkers are below and a GS-rigid linker scheme could be found in FIG. 11B. More specifically the GS-rigid linkers are composed as follows:

N-terminus-$G_3SG_3$-left rigid segment-$G_2SG_2$-right rigid segment-$G_3SG_3$-C-terminus ("$G_3SG_3$" disclosed as SEQ ID NO:96 and "$G_2SG_2$" disclosed as SEQ ID NO:97)

where the rigid segments vary in length and amino acid composition. The following rigid segments have been tested:

```
Right rigid segment in the linkers:
                                    TPAPLPAPLPT      11 AA
                                  TPAPTPAPLPAPLPT    15 AA
                                TPAPLPAPTPAPLPAPLPT  19 AA
                              TPAPLPAPLPAPTPAPLPAPLPT 23 AA Left rigid segments in the linkers:
                                    TPLPAPLPAPT      11 AA  (SEQ ID NO: 5)
                                  TPLPTPLPAPLPAPT    15 AA  (SEQ ID NO: 6)
                                TPLPAPLPTPLPAPLPAPT  19 AA  (SEQ ID NO: 7)
                              TPLPAPLPAPLPTPLPAPLPAPT 23 AA  (SEQ ID NO: 8)

41 aminoacids GS-rigid linker:
GGGSGGGTPLPAPLPAPTGGSGGTPAPLPAPLPTGGGSGGG                              (SEQ ID NO: 1)

49 aminoacids GS-rigid linker:
GGGSGGGTPLPTPLPAPLPAPTGGSGGTPAPTPAPLPAPLPTGGGSGGG                      (SEQ ID NO: 2)

57 aminoacids GS-rigid linker:
GGGSGGGTPLPAPLPTPLPAPLPAPTGGSGGTPAPTPAPTPAPLPAPLPTGGGSGGG              (SEQ ID NO: 3)

65 aminoacids GS-rigid linker:
GGGSGGGTPLPAPLPAPLPTPLPAPLPAPTGGSGGTPAPTPAPTPAPTPAPLPAPLPT (SEQ ID NO: 4)
GGGSGGG
```

Figure 12:
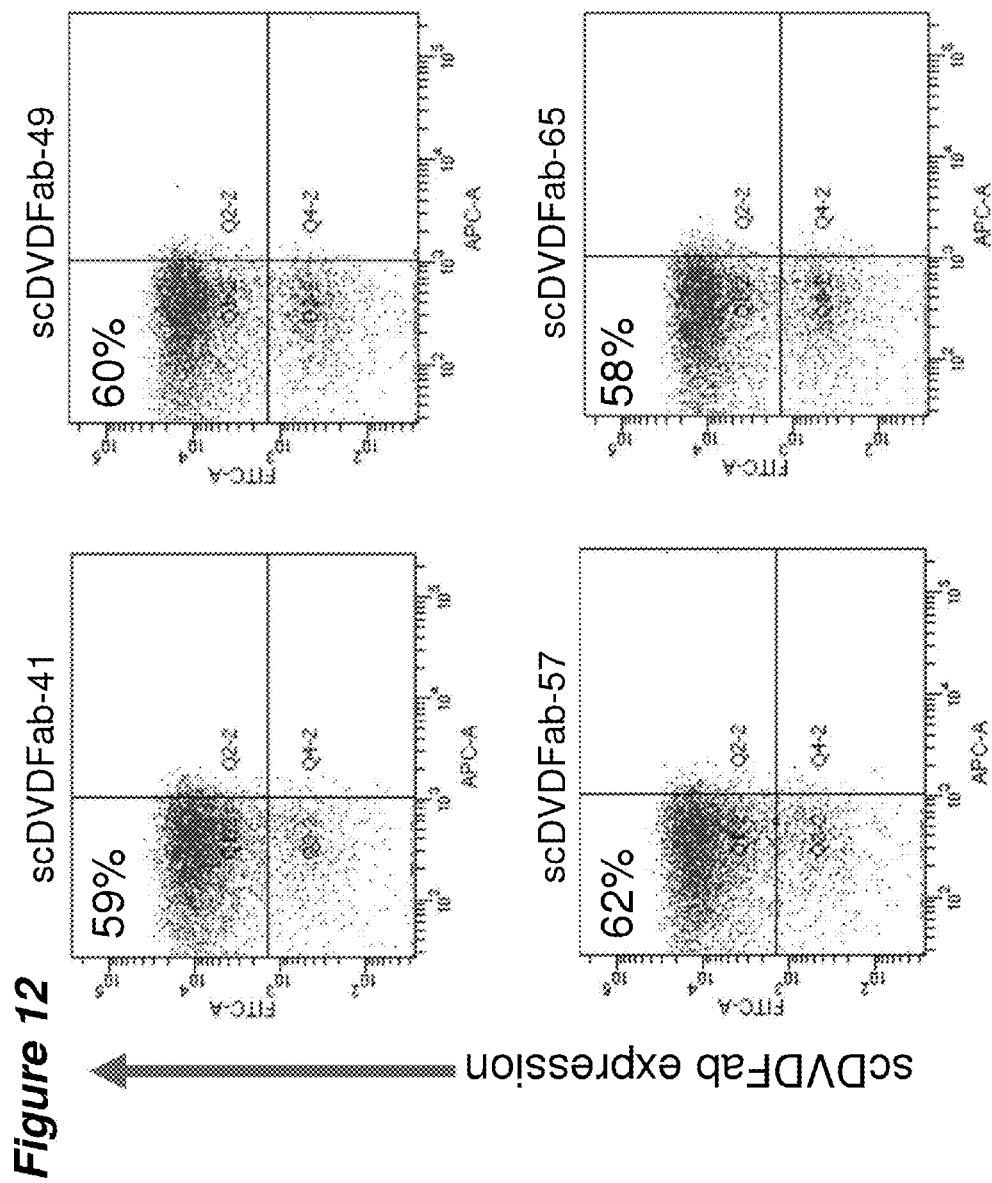
FIG. 12 depicts the results of flow cytometry assays measuring the expression of scDVDFab on the surface of yeast.

EXAMPLE 8 scDVDFab Expression on the Surface of Yeast scDVDFab were expressed on the surface of yeast and the selected peptide tags were suitable for monitoring its expression. ScDVDFab expression on the surface of yeast was monitored by flow cytometry analysis and antibodies were used to detect peptide tags. A DVD-Ig was expressed as scDVDFab on the surface of yeast using pYD vectors and 4 different GS-rigid linkers. The expression of scDVDFab on the surface of yeast was comparable to that observed for scFv molecules reaching more than 50% of the yeast cells expressing the construct (FIG. 12). The length of the GS-rigid linker did not impact the ability of the cells to express the scDVDFab.

EXAMPLE 9

ScDVDFab Retained the Ability of DVD-Ig to Bind Both Targets

Figure 13:
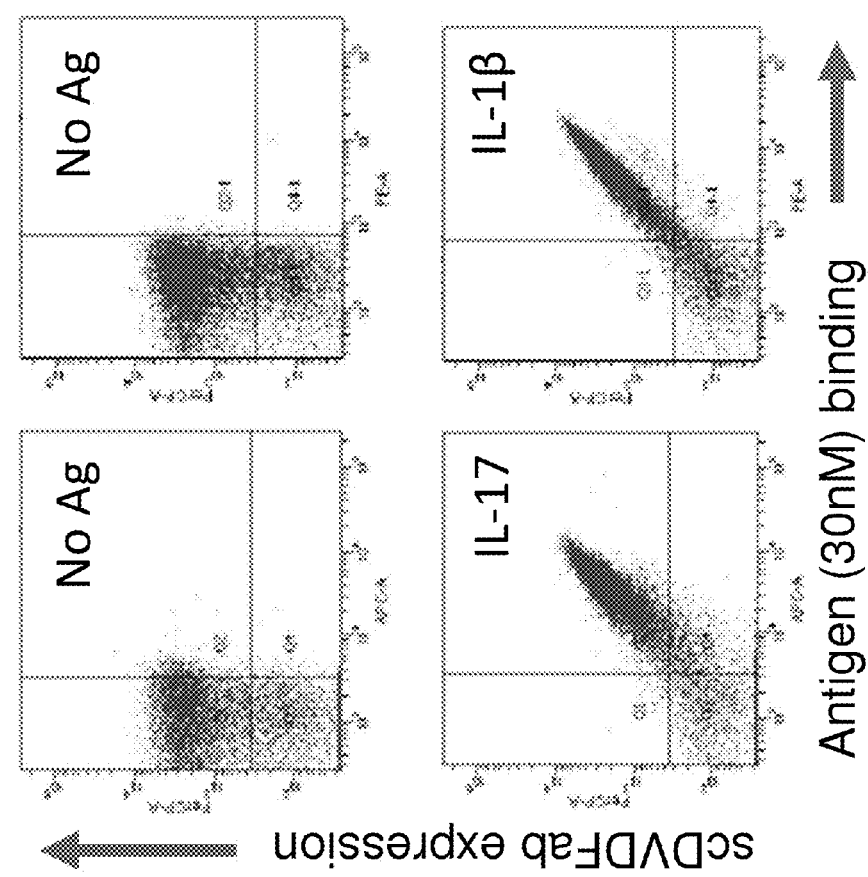
FIG. 13 depicts the results of flow cytometry assays showing that 1B/IL17 scDVDFab expressed on yeast retains its ability to bind both IL1B and/or IL17.

Functional DVD-Ig expressed as scDVDFab maintained its binding capabilities towards its two targets on the surface of yeast. A DVD-Igs was expressed as scDVDFab on the surface of yeast using pYD vectors. Aliquots of the yeast culture were incubated with biotinylated antigens. scDVDFab expression was monitored by purified tag-specific antibodies. Fluorochrome labeled secondary antibodies were used as detection reagents. IL-1B/IL17 scDVDFab retains its ability to bind both IL1B and/or IL17 (FIG. 13).

EXAMPLE 10

Figure 14:
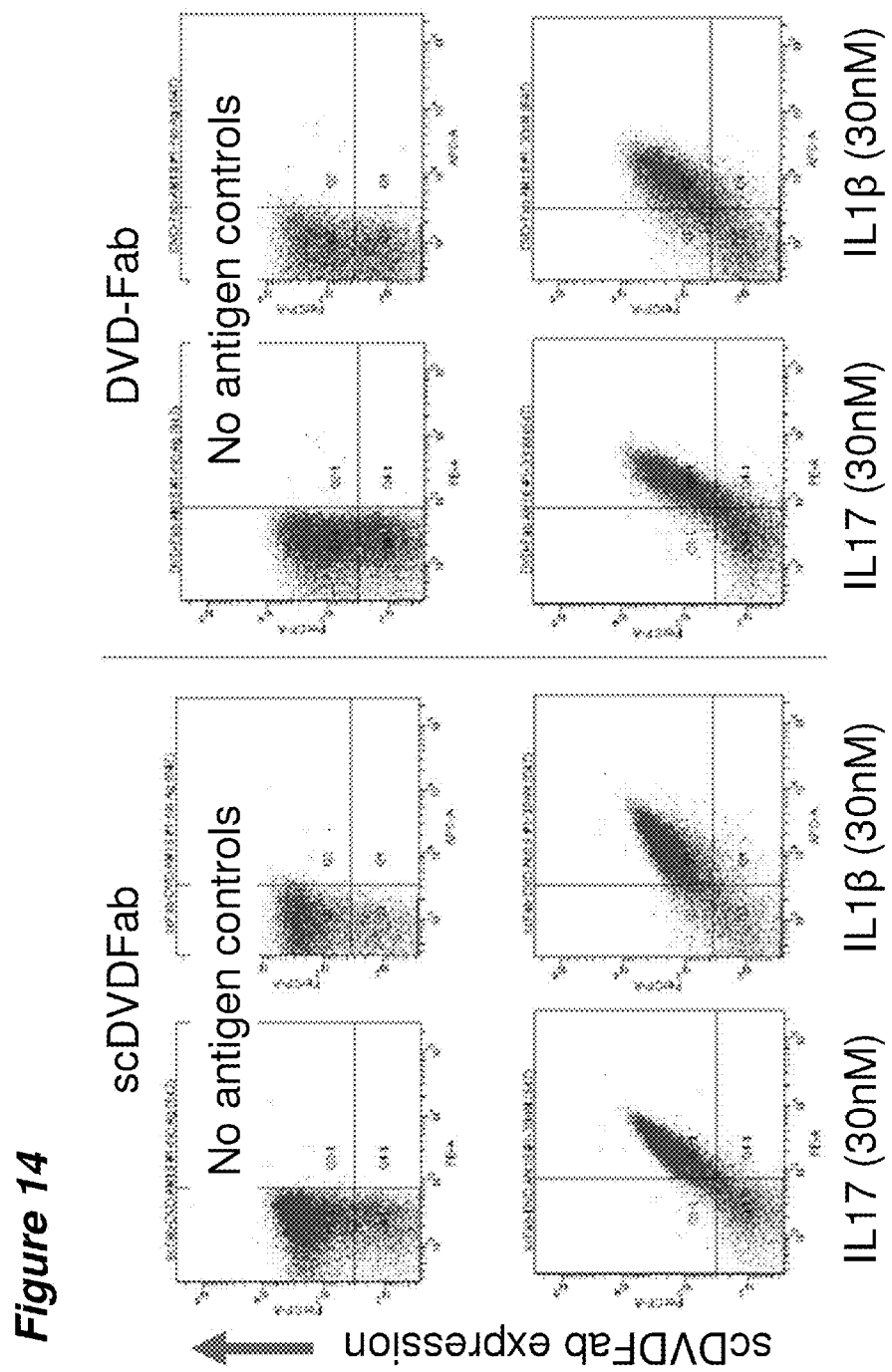
FIG. 14 depicts the results of flow cytometry assays showing that scDVDFab and DVD-Fab had similar binding profiles binding to both IL1B and IL17 on the surface of yeast

Binding to Both Targets is Comparable Between scDVDFab and DVD-Fab Formats Expressed on the Surface of Yeast scDVDFab constructs bound both antigens in a similar way as the DVD-Fab bind them. A DVD-Ig was expressed as scDVDFab and DVD-Fab on the surface of yeast using pYD vectors. Aliquots of the yeast culture were incubated with biotinylated antigens. scDVDFab and DVD-Fab expression was monitored by purified tag-specific antibodies. Fluorochrome labeled secondary antibodies were used as detection reagents. The scDVDFab and DVD-Fab had similar binding profiles binding to both IL1B and 1L17 on the surface of yeast. There is a small increase in the mean fluorescence of scDVDFab compared to DVD-Fab (FIG. 14).

We claim:

1. A diverse library of binding proteins comprising a polypeptide chain having the general formula VH1-(X1)n-VH2-X2-VL1-(X3)n-VL2, wherein VH1 is a first heavy chain variable domain, X1 is a linker with the proviso that it is not a constant domain, VH2 is a second heavy chain variable domain, X2 is a linker, VL1 is a first light chain variable domain, X3 is a linker with the proviso that it is not a constant domain, VL2 is a second light chain variable domain, and n is 0 or 1, wherein the VH1 and VL1, and the VH2 and VL2 respectively combine to form two functional antigen binding sites, and wherein the amino acid sequences of VH1, X1, VH2, X2, VL1, X3, and/or VL2 independently vary within the library.

2. A diverse library of binding proteins comprising a polypeptide chain having the general formula (VL1-(X1)n-VL2-X2-VH1-(X3)n-VH2, wherein VL1 is a first antibody light chain variable domain, X1 is a linker with the proviso that it is not a constant domain, VL2 is a second antibody light chain variable domain, X2 is a linker, VH1 is a first antibody heavy chain variable domain, X3 is a linker with the proviso that it is not a constant domain, VH2 is a second antibody heavy chain variable domain, and n is 0 or 1, wherein the VH1 and VL1, and the VH2 and VL2 respectively combine to form two functional antigen binding sites, and wherein the amino acid sequences of VL1, X1, VL2, X2, VH1, X3, and/or VH2 independently vary within the library.

3. The diverse library of claim 1, wherein each binding proteins further comprises a cell surface anchoring moiety linked to the N or C terminus.

4. The diverse library of claim 3, wherein the anchoring moiety is a cell surface protein.

5. The diverse library of claim 3, wherein the anchoring moiety is Aga2p.

6. The diverse library of claim 1, wherein the polypeptide chain is a scDVD.

7. The library of claim 1, wherein the amino acid sequence of at least one CDR of VH1, VH2, VL1 or VL2 independently varies within the library.

8. The library of claim 1, wherein the amino acid sequence of HCDR3 of VH1, VH2 independently vary within the library.

9. The library of claim 1, wherein the amino acid sequence of HCDR1 and HCDR2 of VH1 or VH2 independently vary within the library.

10. The library of claim 1, wherein the amino acid sequence of HCDR1, HCDR2 and HCDR3 of VH1 or VH2 independently vary within the library.

11. The library of claim 1, wherein the amino acid sequence of HCDR3 of VL1 or VL2 independently vary within the library.

12. The library of claim 1, wherein the amino acid sequence of HCDR1 and HCDR2 of VL1 or VL2 independently vary within the library.

13. The library of claim 1, wherein the amino acid sequence of HCDR1, HCDR2 and HCDR3 of VL1 or VL2 independently vary within the library.

14. The library of claim 1, wherein X1 independently varies within the library and wherein X1 is selected from the amino acid sequences set forth in FIG. 2.

15. The library of claim 1, wherein X2 independently varies within the library and wherein X2 is (G$_4$S)n, where n=1-10 (SEQ ID NO: 53).

16. The library of claim 1, wherein X3 independently varies within the library and wherein X3 is selected from the amino acid sequences set forth in FIG. 2.

17. The library of claim 1, wherein the library of binding proteins share at least 70, 75, 80, 85, 90, 95, 96, 97, 98, or 99 amino acid sequence identity with a reference binding protein.

18. The library of claim 1, wherein VH1 and VH2 of the reference binding protein specifically bind to different antigens.

19. A library of transformed host cells, expressing the diverse library of binding proteins of claim 1.

20. The library of transformed host cells of claim 19, wherein the binding proteins are anchored on the cell surface.

21. The library of transformed host cells of claim 19, wherein the binding proteins are anchored on the cell surface through Aga1p.

22. The library of transformed host cells of claim 19, wherein the host cells are eukaryotic.

23. The library of transformed host cells of claim 22, wherein the host cells are yeast.

24. The library of transformed host cells of claim 22, wherein the yeast is selected from the group consisting of *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus, Pichia pastoris, Rhodotorula* rubra, *Schizosaccharomyces pombe* and *Yarrowia lipolytica*.

25. The library of transformed host cells of claim 22, wherein the yeast is *Saccharomyces cerevisiae*.

26. A method of selecting a binding protein that specifically binds to a target antigen, the method comprising:
   a) providing a diverse library of transformed host cells expressing the diverse library of binding proteins of claim 1;
   b) contacting the host cells with the target antigen; and
   c) selecting a host cell that bind to the target antigen, thereby identifying a binding protein that specifically binds to a target antigen.

27. A method of selecting a binding protein that specifically binds to a first and a second target antigen simultaneously, the method comprising:
   a) providing a diverse library of transformed host cells expressing the diverse library of binding proteins of claim 1;
   b) contacting the host cells with the first and second target antigen; and
   c) selecting a host cell that bind to the first and second target antigen, thereby identifying a binding protein that specifically binds to a first and a second target antigen simultaneously.

28. The method of claim 26, wherein host cells that bind to the first and/or second antigen are selected by Magnetic Activated Cell Sorting using magnetically labeled antigen.

29. The method of claim 26, wherein host cells that bind to the first and/or second antigen are selected by Fluorescence Activated Cell Sorting using fluorescently labeled antigen.

30. The method of claim 26, further comprising isolating the binding protein-encoding polynucleotide sequences from the host cells selected in step (c).

31. A method of producing a binding protein, comprising expressing in a host cell a binding protein that was selected using the methods of claim 26.

* * * * *